United States Patent
Anderson, Jr. et al.

(10) Patent No.: US 6,558,551 B1
(45) Date of Patent: May 6, 2003

(54) METHOD AND SYSTEM FOR GENERATING A HIGH PURITY ELUANT

(75) Inventors: James M. Anderson, Jr., Arlington Heights, IL (US); Raaidah Saari-Nordhaus, Lindenhurst, IL (US); Carl W. Sims, St. Paul, MN (US); Yuri E. Gerner, Mendota Heights, MN (US)

(73) Assignee: Alltech Associates, Inc., Deerfield, IL (US)

( * ) Notice: Subject to any disclaimer, the term of this patent is extended or adjusted under 35 U.S.C. 154(b) by 320 days.

(21) Appl. No.: 09/689,176

(22) Filed: Oct. 11, 2000

Related U.S. Application Data

(63) Continuation of application No. 09/561,631, filed on May 2, 2000, which is a continuation of application No. 08/609,171, filed on Mar. 1, 1996, now Pat. No. 6,093,327, which is a continuation-in-part of application No. 08/486,210, filed on Jun. 7, 1995, now abandoned, which is a continuation-in-part of application No. 08/399,706, filed on Mar. 3, 1995, now abandoned.

(51) Int. Cl.⁷ .................. G01N 30/02; B01D 15/08
(52) U.S. Cl. .......... 210/660; 210/198.2; 210/656; 210/748; 422/70; 436/161; 73/61.52
(58) Field of Search .................. 210/660, 198.2, 210/656, 670, 675, 748; 73/61.52; 436/161; 422/70

(56) References Cited

U.S. PATENT DOCUMENTS

| | | | |
|---|---|---|---|
| 2,980,598 A | 4/1961 | Stoddard | 205/688 |
| 3,557,532 A | 1/1971 | Broerman | 210/656 |
| 3,594,294 A | 7/1971 | Pretorius et al. | 210/656 |
| 3,640,813 A | 2/1972 | Nerenberg | 204/615 |
| 3,694,335 A | 9/1972 | Pretorius et al. | 204/615 |
| 3,722,181 A | 3/1973 | Kirkland et al. | 95/88 |
| 3,795,313 A | 3/1974 | Kirkland et al. | 210/198.2 |
| 3,897,213 A | 7/1975 | Stevens et al. | 422/81 |
| 3,918,906 A | 11/1975 | Small et al. | 436/79 |
| 3,920,397 A | 11/1975 | Small et al. | 436/79 |
| 3,925,019 A | 12/1975 | Small et al. | 436/79 |
| 3,926,559 A | 12/1975 | Stevens | 436/79 |
| 4,242,097 A | 12/1980 | Rich, Jr. et al. | 436/100 |
| 4,265,634 A | 5/1981 | Pohl | 436/161 |
| 4,314,823 A | 2/1982 | Rich, Jr. et al. | 436/100 |
| 4,403,039 A | 9/1983 | Ban et al. | 436/150 |
| 4,455,233 A | 6/1984 | Pohl et al. | 210/635 |

(List continued on next page.)

FOREIGN PATENT DOCUMENTS

| | | |
|---|---|---|
| EP | 0 069 285 A | 1/1983 |
| EP | 0 555 962 A | 8/1993 |

(List continued on next page.)

OTHER PUBLICATIONS

G. I. Mat'tsev et al., "Investigation of Ion Exchange on KU–2 Cationite on Application of an Audio–Frequency Alternating Electrical Field", 3 pages. No month available 1971.

(List continued on next page.)

*Primary Examiner*—Jill Warden
*Assistant Examiner*—John S. Starsiak, Jr.
(74) *Attorney, Agent, or Firm*—Brinks Hofer Gilson & Lione

(57) ABSTRACT

An apparatus and method for electrochemically modifying the retention of a species on a chromatography material is disclosed. The apparatus comprises a housing having an effluent flow channel adapted to permit fluid flow therethrough. The effluent flow channel comprises chromatography material. The apparatus further comprises first and second electrodes positioned such that at least a portion of the chromatography material is disposed between the first and second electrodes, and fluid flow through the apparatus is between, and in contact with, the first and second electrodes.

13 Claims, 19 Drawing Sheets

U.S. PATENT DOCUMENTS

| | | | |
|---|---|---|---|
| 4,459,357 A | | 7/1984 | Jansen et al. ............... 204/520 |
| 4,474,664 A | | 10/1984 | Stevens et al. ............. 210/656 |
| 4,486,312 A | | 12/1984 | Slingsby et al. ............ 210/656 |
| 4,584,075 A | | 4/1986 | Goldstein et al. ........... 204/522 |
| 4,594,135 A | | 6/1986 | Goldstein ................... 204/551 |
| 4,632,745 A | | 12/1986 | Giuffrida et al. ........... 204/632 |
| 4,643,814 A | | 2/1987 | Goldstein ................... 204/522 |
| 4,672,042 A | | 6/1987 | Ross, Jr. et al. ............ 436/161 |
| 4,732,686 A | | 3/1988 | Small et al. ................ 210/656 |
| 4,742,762 A | | 5/1988 | Horstman .................... 98/1.5 |
| 4,747,929 A | | 5/1988 | Siu et al. ................... 204/632 |
| 4,751,004 A | | 6/1988 | Stevens et al. ............. 210/659 |
| 4,751,189 A | | 6/1988 | Rocklin ..................... 436/150 |
| 4,861,555 A | | 8/1989 | Mowery, Jr. ................. 422/70 |
| 4,880,513 A | * | 11/1989 | Davis et al. ................ 204/519 |
| 4,925,541 A | | 5/1990 | Giuffrida et al. ........... 204/524 |
| 4,952,126 A | | 8/1990 | Hanaoka et al. ............. 422/70 |
| 4,981,804 A | | 1/1991 | Hanaoka et al. ............. 436/150 |
| 4,999,098 A | | 3/1991 | Pohl et al. .................. 210/670 |
| 5,032,265 A | | 7/1991 | Jha et al. ................. 210/195.2 |
| 5,045,204 A | * | 9/1991 | Dasgupta et al. .... 204/198.2 X |
| 5,062,961 A | | 11/1991 | Doury-Berthod et al. ... 210/656 |
| 5,068,090 A | | 11/1991 | Connolly ................. 422/82.02 |
| 5,132,018 A | | 7/1992 | Jones et al. ................ 210/656 |
| 5,149,661 A | | 9/1992 | Gjerde et al. ............... 436/178 |
| 5,248,426 A | | 9/1993 | Stillian et al. .............. 210/635 |
| 5,352,360 A | | 10/1994 | Stillian et al. ........... 210/198.2 |
| 5,419,819 A | | 5/1995 | Park ........................ 204/157.2 |
| 5,423,965 A | | 6/1995 | Kunz ......................... 205/702 |
| 5,569,365 A | | 10/1996 | Rabin et al. ................ 204/450 |
| 5,597,734 A | | 1/1997 | Small et al. ................ 436/161 |
| 5,633,171 A | | 5/1997 | Small et al. ................ 436/161 |
| 6,027,643 A | * | 2/2000 | Small et al. ............. 210/198.2 |
| 6,036,921 A | * | 3/2000 | Small et al. .................. 422/70 |
| 6,315,954 B1 | * | 11/2001 | Small et al. ............... 422/68.1 |

FOREIGN PATENT DOCUMENTS

| | | |
|---|---|---|
| JP | 53-116278 | 11/1978 |
| JP | 60-207055 | 3/1984 |
| JP | 52-31958 | 3/1997 |
| WO | WO 94 02227 A | 2/1994 |

OTHER PUBLICATIONS

Z. W. Tian et al., "High–Performance Electrochemical Supressor For Ion Chromatography", *Journal of Chromatography*, vol. 439, pp. 159–163. No month available (1988).

D. L. Strong et al., "Electrodialytic Membrane Suppressor for Ion Chromatography", *Analytical Chemistry*, vol. 61, pp. 939–945. No month available (1989).

D. T. Gjerde et al., "Suspension Postcolumn Reaction Detection Method for Liquid Chromatography", *Analytical Chemistry*, vol. 62, pp. 61–614. No month available (1990).

A. Henshall et al., "A Recent Development in Ion Chromatography Detection: The Self–Regenerating Suppressor". No month available (1992).

Brochure of Applicants' assignee entitled "Improve the Performance of Any Ion Chromatograph", 4 pages, Bulletin #284, Alltech Associates, Inc. No month available (1993).

S. Rabin et al., "New Membrane–Based Electrolytic Suppressor Device for Suppressed Conductivity Detection in Ion Chromatography", *Journal of Chromatography*, vol. 640, pp. 97–109. No month available (1993).

R. S. Nordhaus et al., "Ion Chromatographic Analysis of Anions using a Solid–Phase Chemical Suppressor", 9 pages, Reprinted from *American Laboratory*. No month available (1994).

Brochure entitled "Microparticulate Chemical Suppression with Sarasep Micro Ion Chromatography", 1 page. No date available.

Brochure of Dionex™ entitled "Self–Regenerating Suppressor (SRS)". No month available.

Nafion™ Coats for Electrodes in Liquid Feed Fuel Cells. No month available.

Documents Relating to Presentation Given by Raaidah Saari–Nordhaus and James M. Anderson, Jr. on Jan. 24, 1996 in Caracus, Venezuela.

A. Siriraks et al., "Determination of Anions and Cations in Concentrated Bases and Acids by Ion Chromatography," *Journal of Chromatography*, vol. 640, pp. 151–160 (1993).

* cited by examiner

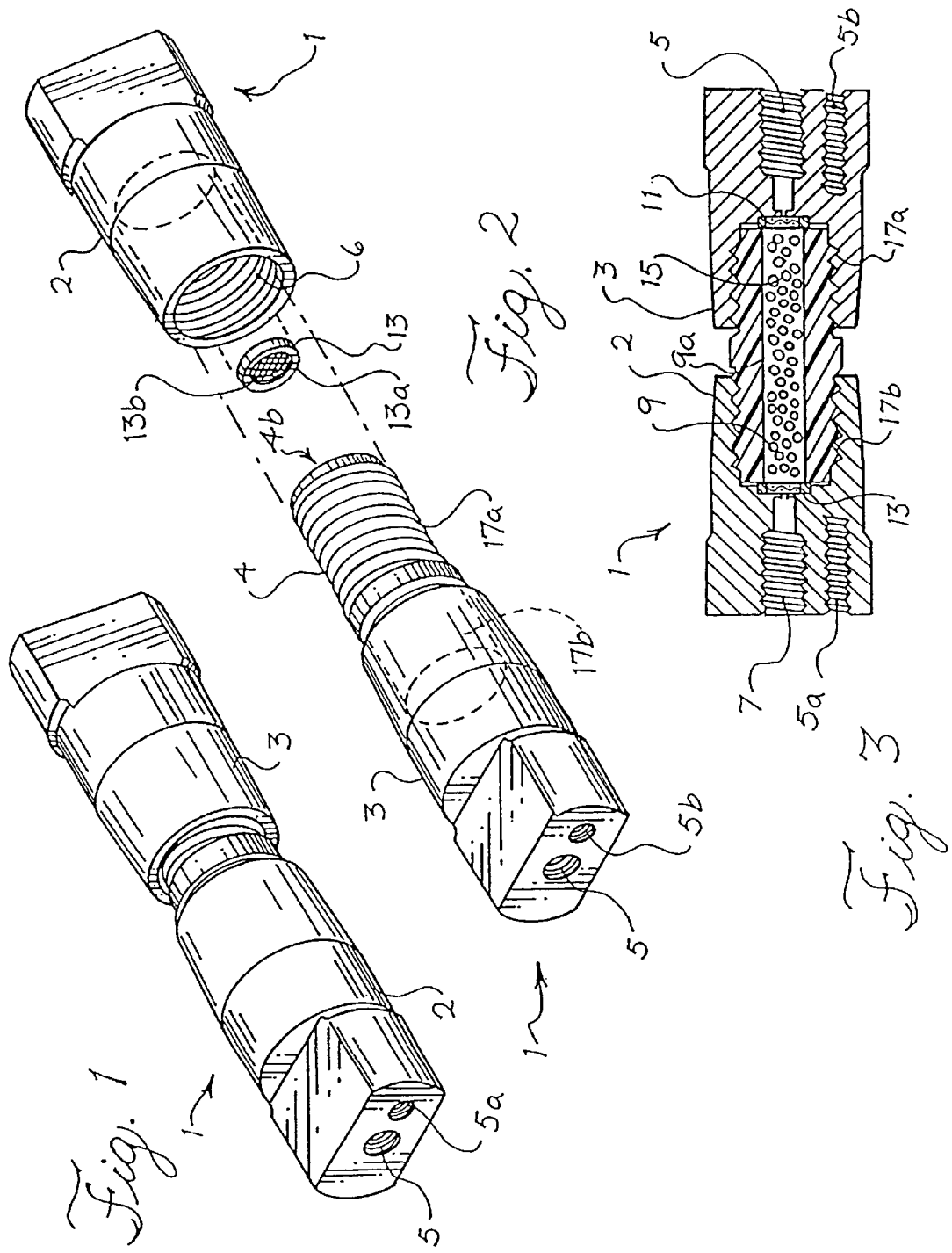

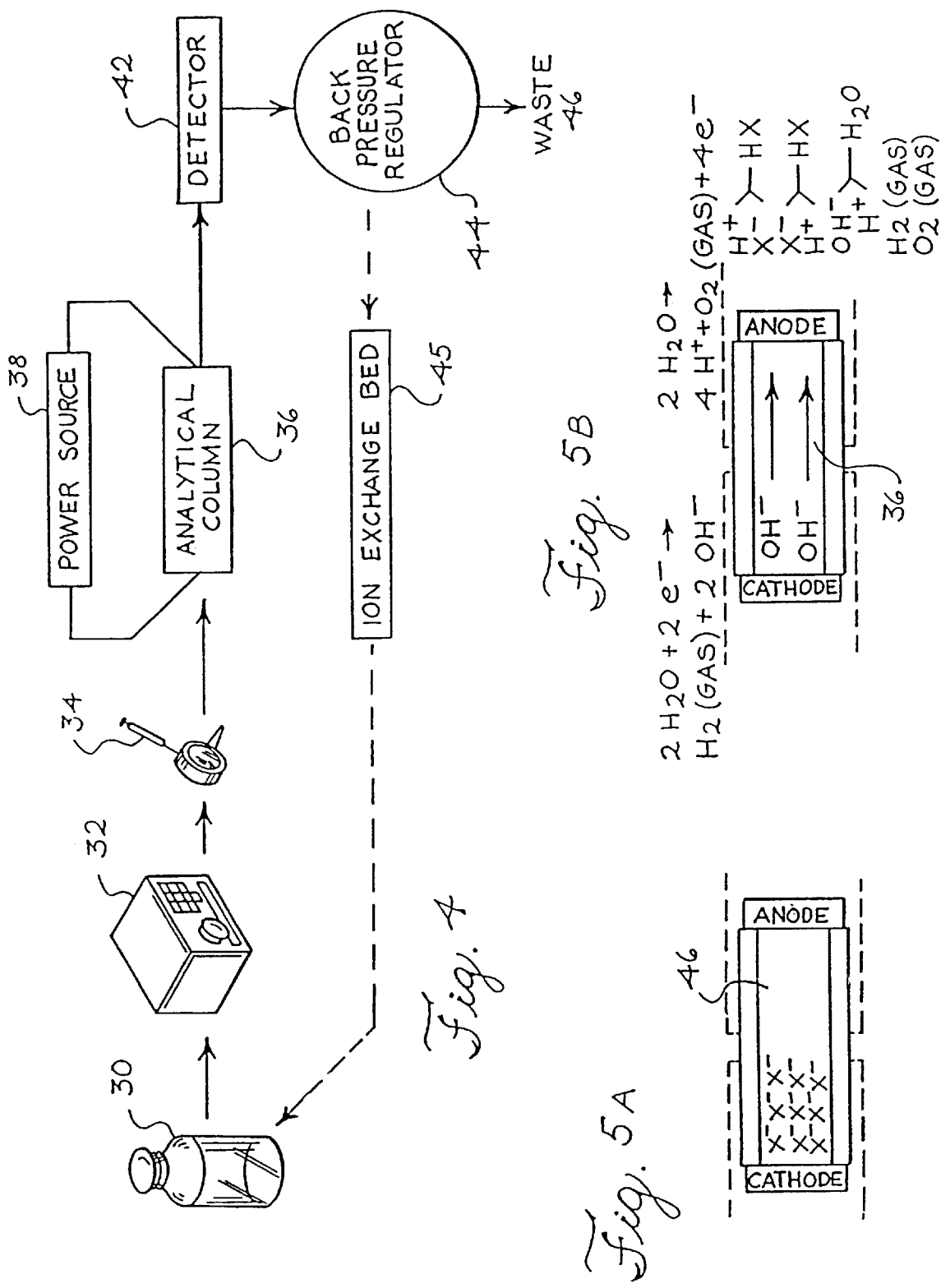

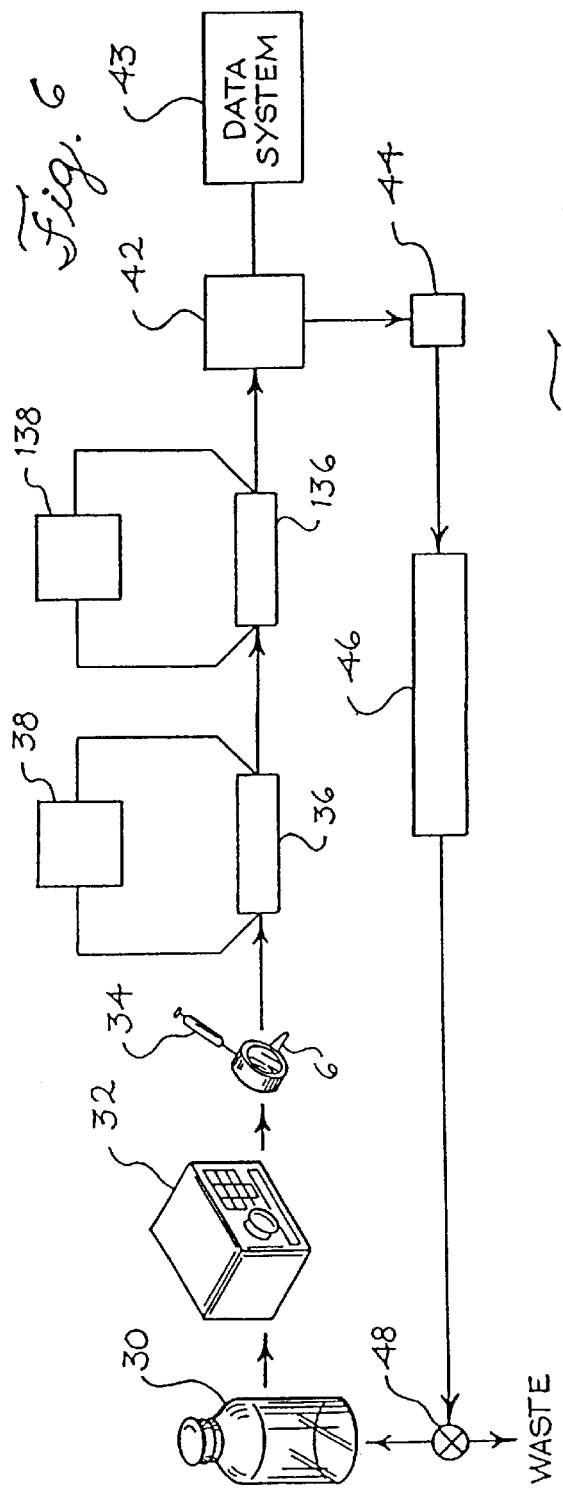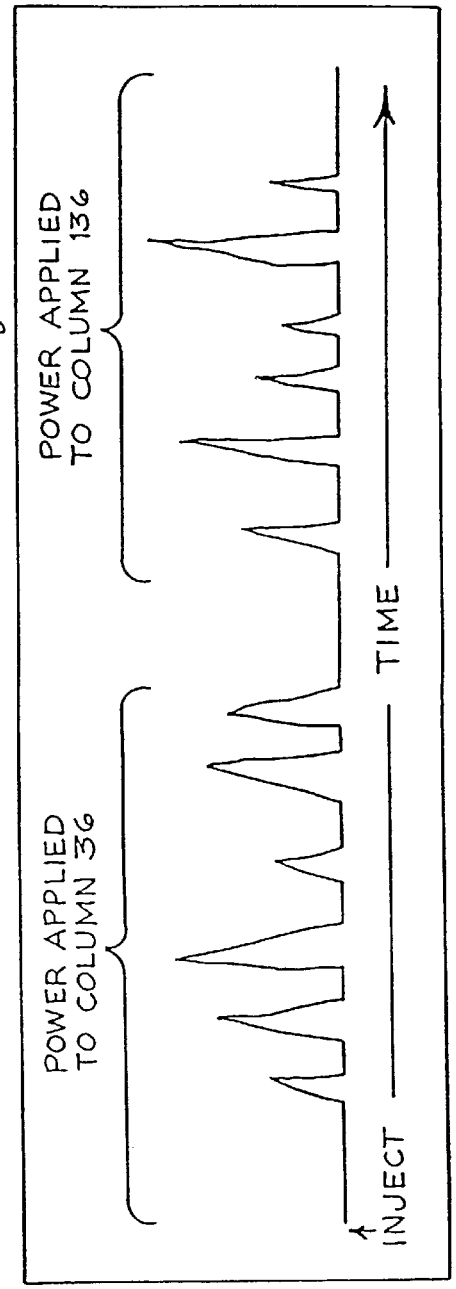

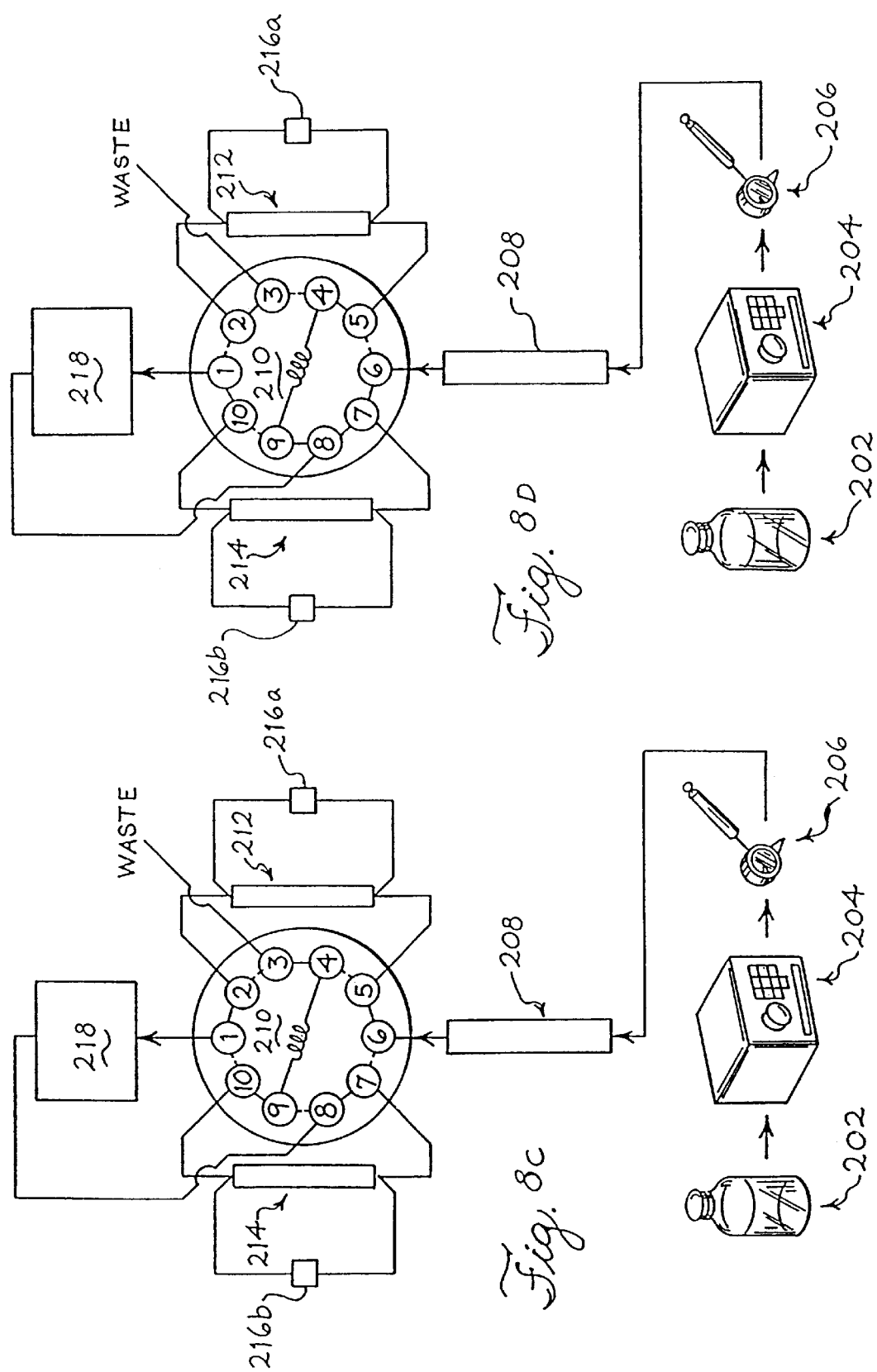

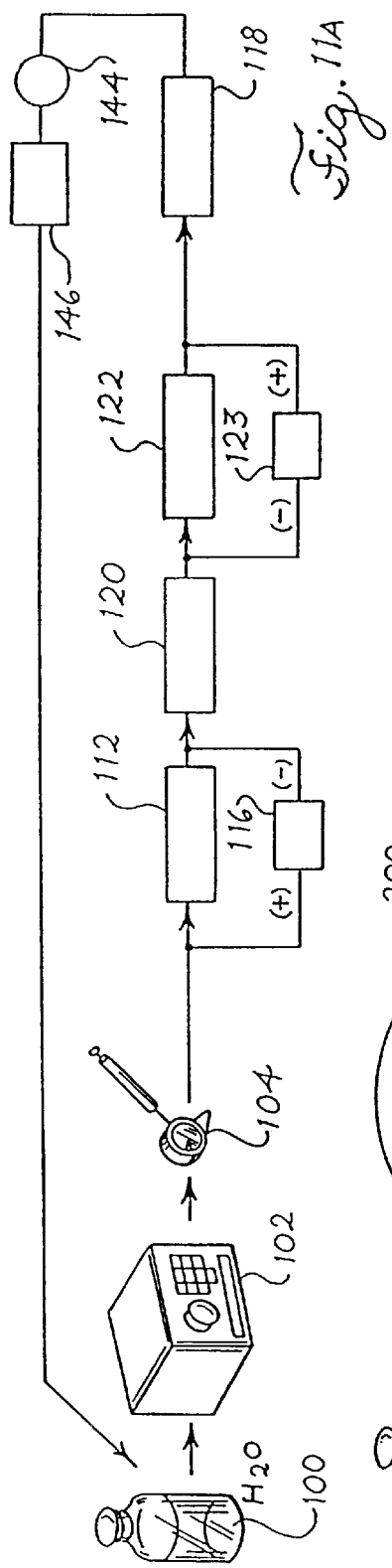
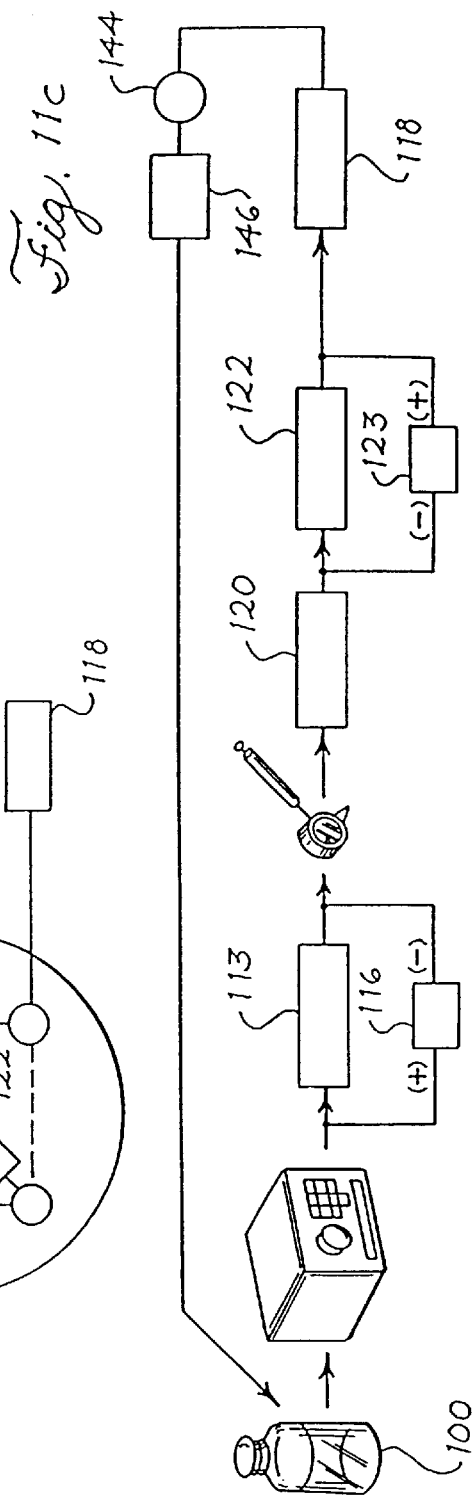
Fig. 11A
Fig. 11B
Fig. 11C

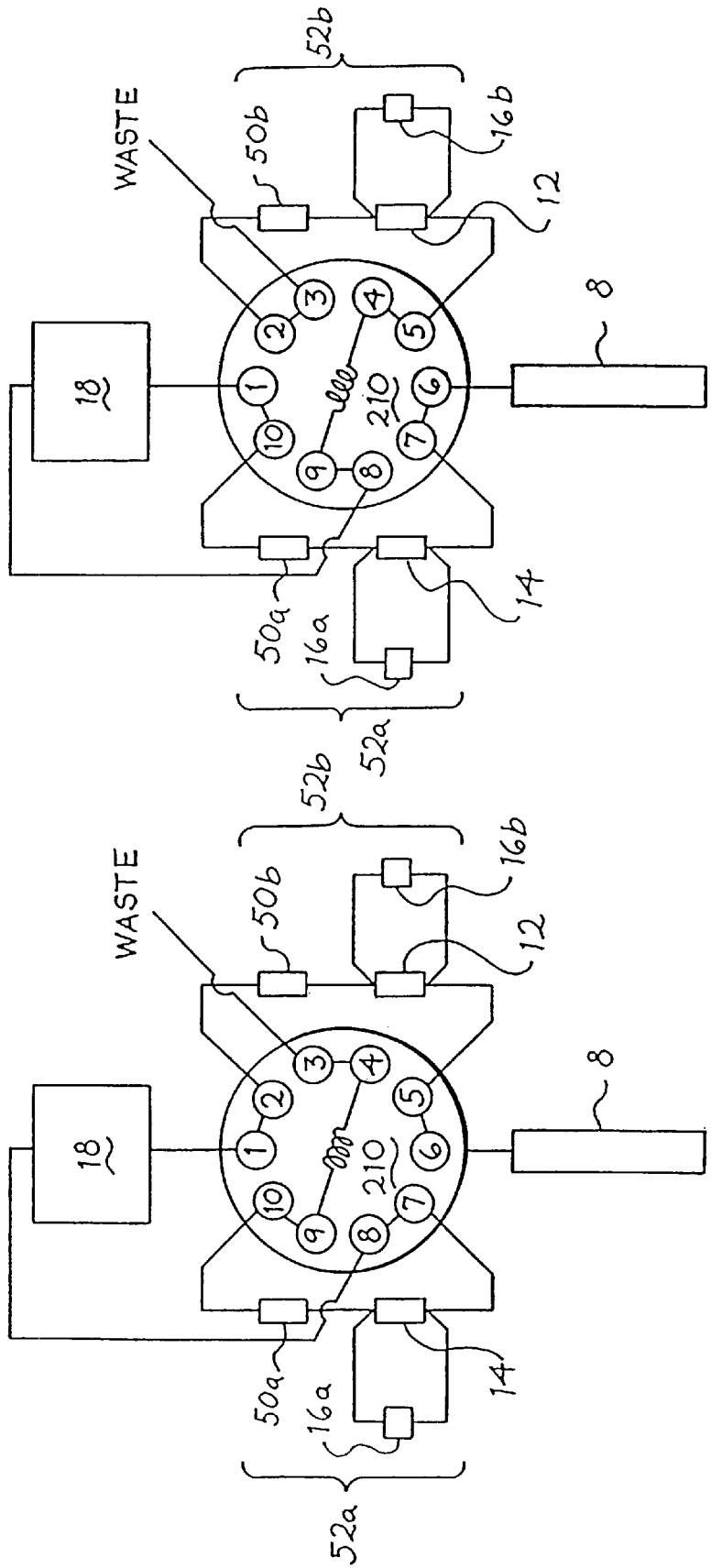

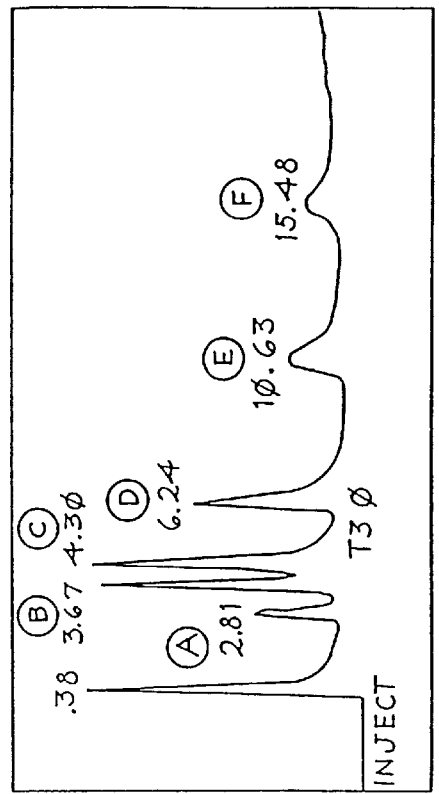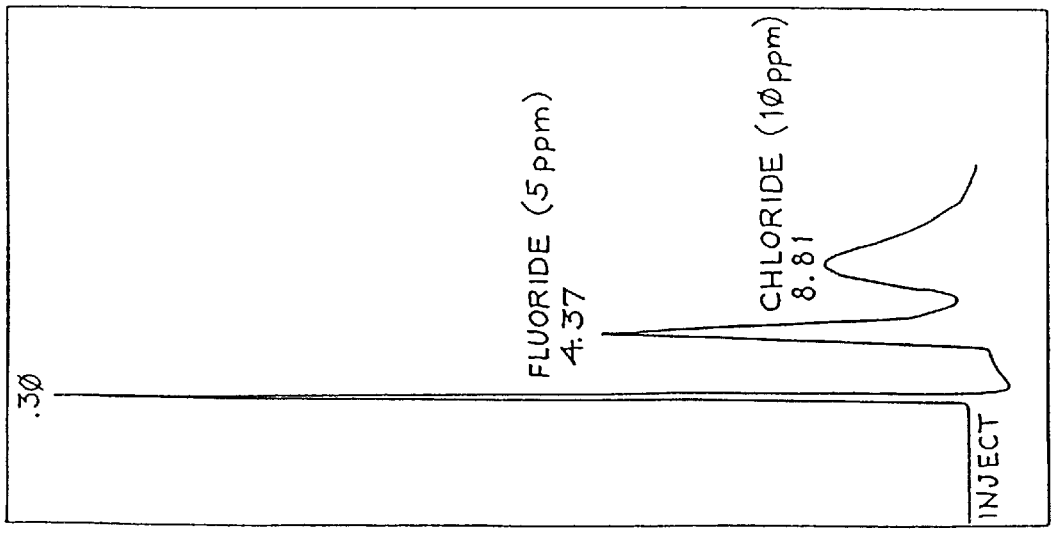

METHOD AND SYSTEM FOR GENERATING A HIGH PURITY ELUANT

PRIOR APPLICATIONS

This application is a continuation of application Ser. No. 09/561,631, filed May 2, 2000, (pending), which is a continuation of application Ser. No. 08/609,171, filed Mar. 1, 1996 now U.S. Pat. No. 6,093,327, which is a continuation in part of application Ser. No. 08/486,210, filed Jun. 7, 1995 now abandoned, which is a continuation in part of application Ser. No. 08/399,706, filed Mar. 3, 1995 now abandoned.

An Appendix consisting of 67 sheets is included in this application. The Appendix contains material which is subject to copyright protection. The copyright owner has no objection to the facsimile reproduction of any one of the sheets of the Appendix, as it appears in the Patent and Trademark patent files or records, but otherwise reserves all copyright rights to this material whatsoever. The pages of the Appendix are incorporated herein by reference as though fully set forth herein.

FIELD OF THE INVENTION

This invention relates to chromatography columns, apparatuses, and methods. In particular, the columns of the present invention can be used as the separation column in electroelution chromatography and are also adaptable for use as a self-regenerating suppressor in suppressed ion chromatography. The columns of the present invention may also be used to separate a wide range of compounds on both an analytical and preparative scale.

BACKGROUND OF THE INVENTION

A. Single Column Ion Chromatography

Single Column Ion Chromatography (SCIC) is a method of ion analysis in which ions are separated in an ion exchange column (e.g., separator column) and subsequently measured by a conductivity detector connected directly to the separator column. In SCIC, special ion exchange resins of low capacity, and eluants with either much higher or much lower equivalent conductance than the ions being measured must be employed. In ion chromatography, sample ions generate a signal at a conductivity detector. The signal is proportional to the sample ion concentration and is the difference in equivalent conductance between the sample ion and the eluant ion. SCIC sensitivity is limited by the difference in equivalent conductance between the sample ions and the eluant ions. This sensitivity is adequate and even preferred for some sample types, especially for cationic samples, where the difference in equivalent conductance between the sample and eluant ions is very large. However, for many other samples, particularly anionic samples, where the difference in equivalent conductance between the sample ions and eluant ions is small, sensitivity can be greatly increased by a second and preferred type of ion analysis called chemically suppressed ion chromatography (SIC).

B. Suppressed Ion Chromatography (SIC)

Suppressed ion chromatography (SIC) is a form of commonly practiced ion analysis characterized by the use of two ion-exchange columns in series followed by a flow through conductivity detector. The first column, called the separation column, separates the ions of an injected sample by elution of the sample through the column using an electrolyte as an eluant, i.e., usually dilute base or acid in deionized water. The second column, called the "suppressor" or "stripper", serves two purposes. First, it lowers the background conductance of the eluant to reduce noise. Second, it enhances the overall conductance of the sample ions. The combination of these two factors significantly enhances the signal to noise ratio, thus increasing sensitivity.

This technique is described in more detail in U.S. Pat. Nos. 3,897,213, 3,920,397, 3,925,019 and 3,926,559. In addition, suitable ion exchange packings for the separation column are described in detail in U.S. Pat. Nos. 3,966,596, 4,101,460 and 4,119,580. A detailed description of ion chromatography is additionally provided in Small et al., "Proceedings of an International Conference on the Theory and Practice of Ion Exchange," University of Cambridge, U.K., July, 1976; and also, Small et al., "Novel Ion Exchange Chromatographic Method Using Conductimetric Detection", Analytical Chemistry, Vol. 47, No. 11, September 1975, pp. 1801 et seq. The foregoing patents and literature publications are fully incorporated herein by reference.

C. Gradient Elution Technology

To separate or elute sample ions retained on an ion-exchange column, an eluant containing co-ions of the same charge of the sample ions is routed through the separation column. The sample co-ions in the eluant partially displace the sample ions on the ion-exchange column, which cause the displaced sample ions to flow down the column along with the eluant. Typically, a dilute acid or base solution in deionized water is used as the eluant. The eluant is typically prepared in advance and routed through the column by either gravity or a pump.

Rather than using a homogenous eluant throughout the separation process, it is sometimes advantageous to use a gradient eluant, i.e., an eluant wherein the concentration of one or more components changes with time. Typically, the eluant starts at a weak eluting strength (e.g. a low concentration of the sample co-ions) and gets stronger (e.g. a higher concentration of the sample co-ions) during the separation process. In this way, easily eluted ions are separated during the weaker portion of the gradient, and ions that are more difficult to elute are separated during the stronger portion of the gradient. The eluant concentration changes during the gradient and suppressing or balancing the concurrent change in background conductance is required so the sample signal may be discriminated from the background signal. An example of such gradient elution techniques are disclosed in U.S. Pat. Nos. 4,751,189 and 5,132,018, the entire disclosures of which are incorporated herein by reference.

While the above patents utilize solutions prepared in advance to form a gradient eluant, U.S. Pat. No. 5,045,204 to Dasgupta et al. uses electrochemical methods to generate a high purity eluant stream that may flow directly to the separation column as it is produced, and which may be generated as a gradient. In the Dasgupta patent, a product channel is defined by two permselective membranes and is fed by a source of purified water. One of the permselective membranes only allows the passage of negatively charged hydroxide ions, which are generated on the side of this membrane opposite the product channel by the electrolysis of water at a cathode. The hydroxide ions are driven by an electric field through the membrane into the product channel in an amount corresponding to the strength of the electric field. The other permselective membrane only allows the passage of positively charged ions. On the side of this membrane opposite the product channel there is a source channel, which is continuously fed with a NaOH solution and in which an anode is positioned. The $Na^+$ ions are driven by the electric field through the membrane into the product channel in an amount corresponding to the strength of the electric field. By this process, a high purity sodium hydroxide (NaOH) solution is produced. This solution may be used as the eluant for a chromatography column, and the concentration of this eluant may be varied during the chromatographic separation by varying the strength of the electric field, thereby generating a gradient eluant.

The foregoing methods of elution ion chromatography suffer from certain disadvantages, however. Among these disadvantages is that an outside source of eluant or eluant counter-ions is required. Also, after eluting the sample ions from the chromatography column, all of these eluants require suppression in order to provide an accurate quantitative analysis of the sample ions. Finally, in general practice, all of the above methods of eluting are only applicable to one of either cation or anion sample ions within a single sample run. If one wishes to analyze both the cations and anions from a single sample, two chromatographic separations must be performed using either two apparatuses and two distinct eluants, or a single instrument with two or more columns and complex switching valves.

D. Prior Suppressor Technology

Chemical suppression for IC serves two purposes. First, it lowers the background conductance of the eluant to reduce baseline noise. Second, it enhances the overall conductance of the sample ions to increase the signal.

The combination of these two factors significantly enhances the signal-to-noise ratio, and increase the detectivity of the sample ions. For example, in anion analysis, two ion-exchange reactions take place in a suppressor column when the eluant comprises sodium hydroxide and the ion exchange packing material in the suppressor column comprises exchangeable hydronium ions:

1) Eluant: $NaOH + Resin-SO_3^-H^+ \rightarrow Resin-SO_3^-Na^+ + H_2O$

2) Analyte: $NaX + Resin-SO_3^-H^+ \rightarrow Resin-SO_3^-Na^+HX$
where X=anions ($Cl^-$, $NO_2^-$, $Br^-$, etc.)

The relatively high conductivity sodium hydroxide eluant is converted to the relatively low conductivity water when the sodium ions from the eluant displace the hydronium ions on the ion exchange packing material in the suppressor. The sample anions are converted from their salt form into their more conductive acid form by exchanging their counter-ions for hydronium ions in the suppressor. The eluant is preferably a solution of any salt that forms a weakly conductive acid after going through the suppressor. Examples of such eluants in anion analysis include sodium hydroxide, sodium carbonate, or sodium tetraborate solutions.

Various suppressor devices that operate on the above principles have been used for IC. These include:

1. Packed-Bed Suppressors

Packed-Bed Suppressors were introduced in about 1973 (see, for example, U.S. Pat. Nos. 3,918,906, 3,925,019, 3,920,397, 3,926,559, 4,265,634, and 4,314,823, the entire disclosures of which are incorporated herein by reference). These suppressors consist of large columns containing strong acid cation-exchange resins in hydronium form (for anion analysis). In order to house enough resin, these columns are very large (i.e., 250 mm×7.8 mm). However, these columns have a large dead volume, which causes considerable peak dispersion and broadening. This, in turn, results in a loss of chromatographic efficiency. Moreover, after several hours of operation, the resin bed becomes exhausted (all the hydronium ions on the exchange sites are replaced by the sample and the eluant counterions). The suppressor column must then be taken off-line and regenerated by flushing the column with an acid to regenerate the hydronium ion exchange sites in the resin bed. The regeneration of the suppressor column, of course, is time consuming and interrupts the analysis.

Another disadvantage of these packed bed suppressors is that weakly ionized species such as organic acids can penetrate the protonated cation exchange sites and interact by inclusion within the resin bed. This causes variable retention times and peak areas as the suppressor becomes exhausted. Also, some ions can undergo chemical reactions in the suppressor. For example, nitrite has been shown to undergo oxidation in these prior art packed bed suppressors leading, to variable recovery and poor analytical precision.

2. Hollow-Fiber Membrane Suppressors

In about 1982, hollow fiber membrane suppressors were introduced (see, for example, U.S. Pat. Nos. 4,474,664 and 4,455,233, the entire disclosures of which are incorporated herein by reference). Hollow fiber membrane suppressors were designed to overcome the drawbacks of the packed bed suppressors. The hollow fiber membrane suppressors consist of a long, hollow fiber made of semi-permeable, ion-exchange material. Eluant passes through the hollow center of the fiber, while a regenerating solution bathes the outside of the fiber. Suppressor ions cross the semi-permeable membrane into the hollow center of the fiber, and suppress the eluant. The regenerating solution provides a steady source of suppressor ions, allowing continual replacement of the suppressor ions as they pass to the eluant flow channel in the hollow center of the fiber. The main advantage of the hollow fiber design is that the chromatography system can be continuously operated because there is no need to take the suppressor off-line for regeneration, as is the case with the packed bed suppressors.

However, the hollow fiber design introduced new problems. The small internal diameter of the fibers reduces the surface area available for ion exchange between eluant and the regenerant. This limits the suppression capability of the hollow fiber suppressors to low flow rates and low eluant concentrations. Additionally, because the fiber is bathed in the regenerant solution, the counterion of the suppressor ions can leak into the eluant channel, and cause higher background conductivity and baseline noise at the detector.

3. Flat-Sheet Membrane Suppressors

Flat-sheet membrane suppressors were introduced in about 1985 (see, for example, U.S. Pat. Nos. 4,751,189 and 4,999,098, the entire disclosures of which are incorporated herein by reference). In these suppressors, the ion exchange tubing in the hollow-fiber suppressor is replaced with two flat semi-permeable ion exchange membranes sandwiched in between three sets of screens. The eluant passes through a central chamber which has ion exchange membrane sheets as the upper and lower surfaces. The volume of the eluant chamber is very small, so band broadening is minimal. Since the membrane is flat, the surface area available for exchange between the sample counterions and the suppressor ions in the regenerant is greatly increased. This increases the suppression capacity allowing high flow rates, high eluant concentration, and gradient analyses. Preferably, the regenerant flows in a direction counter to the sample ions over the outer surfaces of both membranes, providing a constant supply of suppressor ions.

A major drawback, however, of membrane suppressors is that they require a constant flow of regenerant to provide continuous suppression/operation. This consumes large volumes of regenerant and produces large volumes of chemical waste, significantly increasing operating cost. An additional pump or device is required to continuously pass the regenerant through the suppressor, increasing the instrument's complexity and cost while reducing reliability. Also, organic compounds can irreversibly adsorb onto the hydrophobic ion-exchange membrane, reducing its efficiency to the point where it requires replacement (membranes are typically replaced every six months to two years). Finally, the membranes are very thin and will not tolerate much backpressure. Thus, membrane rupture is a concern anytime downstream backpressure increases due to blockages.

4. Solid Phase Chemical Suppressor (SPCS)

Alltech Inc., the assignee of the present application, developed solid phase chemical suppressors (SPCS) in about 1993, which were essentially an improved version of the original packed bed suppressors. Problems associated with the original packed bed suppressors, such as band broadening, variable retention time and peak area, and the oxidation of nitrite in the suppressor, were greatly reduced. The Alltech SPCS uses disposable cartridges containing ion exchange packing material comprising suppressor ions as the suppressor device. The inexpensive cartridges are simply discarded and replaced with a new cartridge when the suppressor ions are exhausted. Thus, no regeneration is required, thereby eliminating the need for expensive or complex systems for regenerating suppressor ions.

In Alltech's SPCS system, a 10-port switching valve and two disposable suppressor cartridges are typically employed. The effluent from the analytical column flows through one cartridge at a time. While one cartridge is being used, the suppressed detector effluent (typically water or carbonic acid) flows through the other suppressor cartridge to pre-equilibrate the cartridge. This reduces the baseline shift due to conductance change when the valve is switched to the other suppressor cartridge. When all the suppressor ions from one cartridge are replaced by the eluant and sample counterions, the valve is switched, placing the second cartridge in the active position, and the exhausted suppressor cartridge is replaced. This allows continuous operation. However, the Alltech system still requires someone to switch the valve manually when the first cartridge is exhausted. Each cartridge typically provides between 6 to 9 hours of operation, and thus fully unattended or overnight operation might not be possible in certain applications with the Alltech SPCS system.

5. Electrochemical Suppression

Electrochemical suppressors were introduced in about 1993. These suppressors combine electrodialysis and electrolysis in a flat-sheet membrane suppressor column similar to those described under heading section 3 above (see U.S. Pat. Nos. 4,459,357 and 5,248,426, the entire disclosures of which are incorporated herein by reference).

For example, U.S. Pat. No. 5,248,426 to Stillian et al. discloses a suppressor which contains a central chromatography effluent flow channel bordered on both sides by ion exchange membranes with exchangeable ions of the opposite charge of the sample ions. On the side of each membrane opposite the effluent flow channel are first and second detector effluent flow channels. The sample ions and eluant are routed through the chromatography effluent flow channel, and the water-containing detector effluent is routed through the detector effluent flow channels in the suppressor. An electrode is positioned in both of the detector effluent flow channels.

By energizing the electrodes, an electrical potential is generated in the suppressor transverse to the liquid flow through the chromatography flow channel. When the water-containing detector effluent contacts the energized electrodes, it undergoes electrolysis. In anion analysis for example, the suppressor hydronium ions generated at the anode in a first detector-effluent channel are transported across the ion exchange membrane into the chromatography effluent flow channel, where they combine with the sample anions to form the highly conductive acids of the sample anions. The suppressor hydronium ions also combine with the hydroxide ions in the eluant (in anion analysis) to convert the eluant into the relatively non-conductive water. At the same time, the eluant and sample counterions are transported from the chromatography effluent channel across the ion exchange membrane into a second detector effluent flow channel where they combine with the hydroxide ions generated by the electrolysis of the water-containing detector effluent at the cathode in the second detector effluent flow channel. The resulting bases of the eluant counterions are then routed to waste.

Thus, the electric field generated in the suppressor column disclosed in Stillian et al. simultaneously generates suppressor ions and promotes ion-flow between the electrodes in a direction transverse to the fluid flow through the suppressor. The mass transport of ions is across a first ion exchange membrane from a first detector effluent flow channel to the chromatography effluent flow channel, and across a second ion exchange membrane to a second detector effluent flow channel.

Although the electrochemical suppressor device disclosed in Stillian et al. offers certain advantages (i.e. no separate regenerant source is required), it still suffers from certain disadvantages. Irreversible adsorption of organic components and membrane breakage under pressure may still occur in the apparatus and method disclosed in Stillian. Also, the method of electrochemical suppression disclosed in Stillian can only be used to analyze solely anions or solely cations in any one sample. Finally, the Stillian method does not work well with electroactive eluants or organic solvents. Electroactive eluants, such as hydrochloric acid, commonly employed as an eluant for cation analysis, undergo electrochemical reaction in the suppressor producing by-products that damage the membrane. Also, certain organic eluant components such as methanol undergo electrochemical reaction in the electrochemical suppressor producing by-products that are conductive and which interfere with the detection of sample ions. Such electroactive eluant systems may not be effectively employed in the Stillian method.

The column, apparatuses, and methods of the present invention reduce or avoid many of the foregoing problems.

SUMMARY OF THE INVENTION

In one aspect of the present invention, the foregoing disadvantages are overcome. The column of the present invention can be used in apparatuses and methods for generating an eluant in-situ that does not require an outside source of sodium or other electrolytes. Additionally, the column of the present invention can be used in apparatuses and methods that generate a self-suppressing eluant and, therefore, a second suppressor column is not required. Moreover, the column of the present invention can be adapted for use in apparatuses and methods for analyzing both cations and anions in a single sample run.

In one embodiment of the present invention, a housing is provided. The housing has an effluent flow channel adapted to permit fluid flow through the housing. The housing further contains chromatography packing material disposed in the effluent flow channel. The housing also contains first and second electrodes which are positioned such that at least a portion of the chromatography packing material is disposed between the first and second electrodes, and fluid flow through the housing is from one of the first or second electrodes to the other.

In another aspect of the invention, an apparatus for electrochemically modifying the retention of a species on chromatography material is provided. The apparatus has a housing, which comprises an effluent flow channel. The effluent flow channel comprises chromatography material, and the effluent flow channel is adapted to permit fluid flow therethrough. The apparatus further comprises a first electrode and a second electrode. These first and second electrodes are positioned such that at least a portion of the chromatography material is disposed between the first and second electrodes, and the fluid flow through the effluent flow channel is between, and in contact with, the first and second electrodes. Also, the apparatus further comprises a power source connected to the first and second electrodes.

In yet another aspect of the invention, a method of electrochemically modifying the retention of a compound or species on a chromatography material is provided. According to this method, an effluent flow channel is provided comprising a stationary phase containing chromatography material on which the compound or species is retained. A first and a second electrode are also provided, and the electrodes are positioned such that at least a portion of the chromatography material is disposed between the first and second electrodes. A mobile phase comprising an eluant is further provided. The eluant is flowed between, and in contact with, the first and second electrodes thereby electrochemically modifying the eluant. The modified eluant is flowed to the chromatography material, which modifies the retention of the compound or species on the chromatography material.

The foregoing housing and apparatus may be used as a chromatography column, a self-regenerating suppressor, and in various chromatography apparatuses according to various embodiments of the present invention. The apparatus of the present invention may also be used in various methods of separating ions, proteins, and other compounds. The apparatus of this invention may also be used in methods of generating a high purity eluant, and for generating a gradient in gradient elution chromatography.

These and other advantages of the invention, as well as the invention itself, will be best understood with reference to the attached drawings, a brief description of which follows, along with the detailed description of the invention provided herein.

BRIEF DESCRIPTION OF THE DRAWINGS

FIG. 1 is a perspective view of a preferred column of the present invention.

FIG. 2 is an exploded view of the column illustrated in FIG. 1.

FIG. 3 is a cross-sectional view of the column illustrated in FIG. 1.

FIG. 4 is a schematic view of a chromatography apparatus for use in a method of electroelution chromatography.

FIGS. 5A and 5B are schematic views of the chromatography column of FIG. 1 showing ion exchange when the column is used in a method of electroelution chromatography.

FIG. 6 is a schematic view of a chromatography apparatus for use in a method of electroelution chromatography.

FIG. 7 is an illustrative chromatogram using the chromatography apparatus depicted in FIG. 6 in a method of electroelution chromatography where anions and cations in the same sample are detected.

FIGS. 8A–8D are schematic views of chromatography apparatuses where the column of FIG. 1 is used as a solid phase chemical suppressor.

FIGS. 11A and 11B are schematic views of a chromatography apparatus where two columns of the present invention are used as an eluant generating column to generate a high purity eluant, and as a solid phase chemical suppressor, respectively.

FIG. 11C is a schematic view of a chromatography apparatus where the column of FIG. 1 is used as a solid phase chemical suppressor.

FIGS. 12A and 12B are schematic views of a chromatography apparatus where the column of FIG. 1 is used in a hydrophobic suppressor unit.

FIG. 17 is a chromatogram of a sample containing ions using a column according to one embodiment of the present invention.

FIG. 18 is a chromatogram of a sample containing ions using a column according to one embodiment of the present invention.

DETAILED DESCRIPTION OF THE DRAWINGS AND PRESENTLY PREFERRED EMBODIMENTS

Figure 8A:
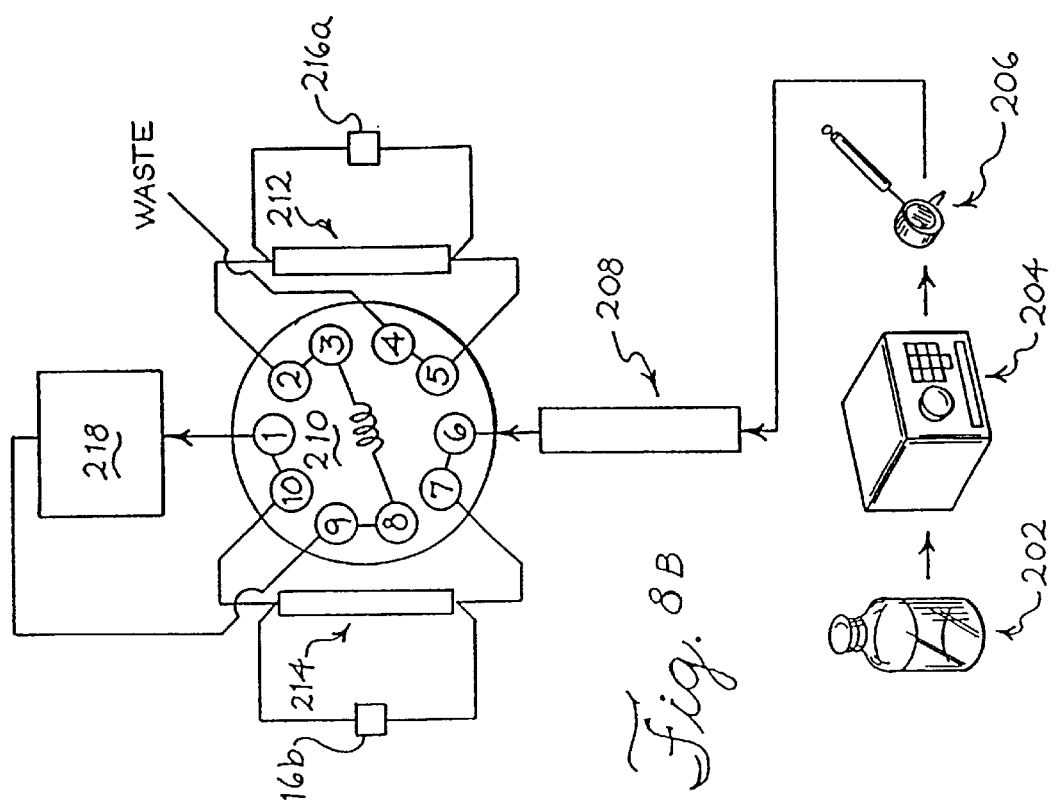
Figure 8B:
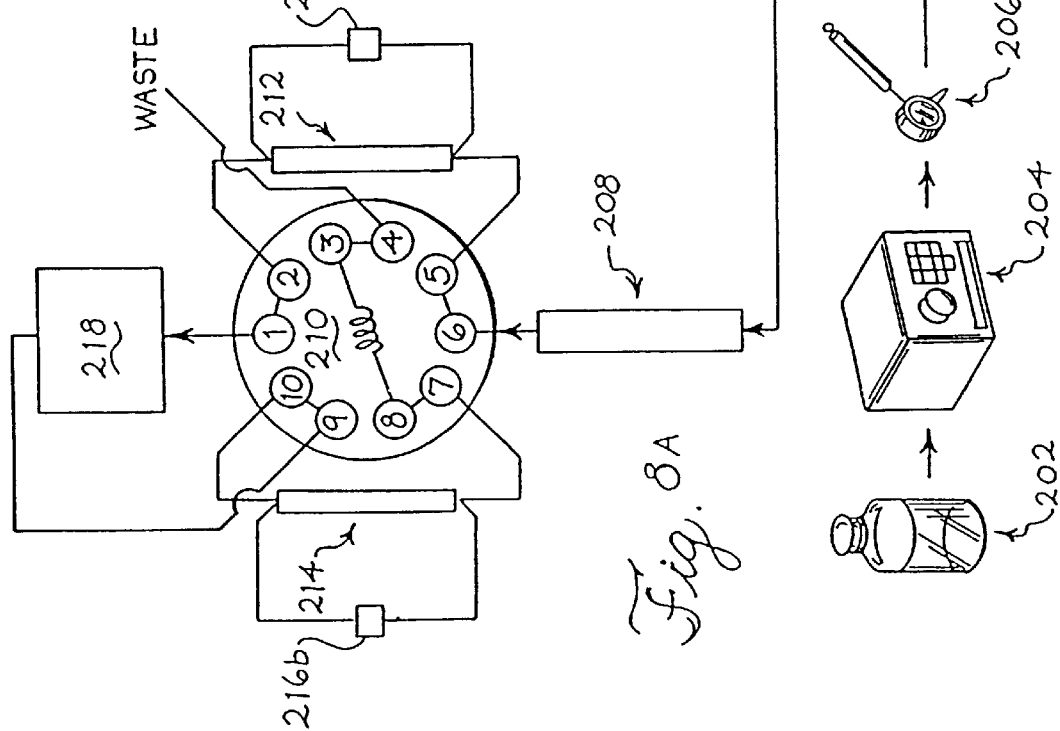

The preferred column of the present invention is especially adapted for use in chromatography apparatuses and methods. With reference to FIGS. 1–3, the preferred chromatography column comprises a housing 1. The housing 1 consists of female end fitting 2 and male end fitting 3. The female end fitting and the portion of the male end fitting other than arm 4 are preferably made from a conductive material. Preferably, these pieces are made from titanium or stainless steel coated with inert material. The male end fitting 3 has a threaded arm 4 secured thereto. The arm 4 of the male end fitting 3 further comprises a cavity 4b. The threaded arm is preferably made from a non-conductive, water proof plastic material. The arm 4 of male end fitting 3 is most preferably made from polyetheretherketone (PEEK). The female end fitting 2 also has a cavity 6. The cavity 6 is preferably threaded and adapted to receive the threaded arm 4 of male end fitting 3.

Housing 1 is easily assembled by releasably securing arm 4 of male end fitting 3 in the cavity 6 of the female end fitting 2. This is accomplished by simply screwing the threaded arm 4 of the male end fitting 3 into the cavity 6 of female end fitting 2. Similarly, the housing 1 may be just as easily dismantled by unscrewing the threaded arm 4 of male end fitting 3 from the cavity 6 of female end fitting 2. When the housing 1 is assembled, the cavity 4b of the arm 4 of male end fitting 3 provides part of an effluent flow channel 9, which is adapted to permit fluid flow through the housing 1.

The male end fitting 3 has an opening 5, which is adapted to permit fluid to enter or exit the housing 1. The female end fitting 2 also has an opening 7 which is adapted to permit fluid to enter or exit the housing 1. Preferably, openings 5 and 7 are threaded for easy connection to fluid lines in the chromatography apparatuses and methods described herein. Extending from the opening 5 of male end fitting 3 to opening 7 of female end fitting 3 when the housing 1 is assembled is the effluent flow channel 9.

The housing 1 further preferably comprises first and second electrodes 11 and 13. Preferably, first and second electrodes 11 and 13, respectively, are positioned at opposite ends of the effluent flow channel 9, and are positioned such that the fluid flow through the housing 1 is from one of the first or second electrodes to the other. In the most preferred embodiment, the electrodes 11 and 13 are positioned near the openings 5 and 7 of the male end fitting 3 and female 2 end fitting, respectively, of the housing 1.

The housing 1 further comprises chromatography packing material 15 disposed within the effluent flow channel 9. The chromatography packing material 15 is selected as discussed with respect to the various embodiments discussed below. Preferably, at least a portion of the chromatography packing material is disposed between the first and second electrodes. However, in an alternative embodiment of the present invention, those skilled in the art will appreciate that, instead of using chromatography packing material 15, the effluent flow channel 9 may be defined by chromatography material (not shown). For example, chromatography material (not shown) may be coated on the wall 9a of the effluent flow channel 9.

Alternatively, the wall 9a of effluent flow channel 9 may comprise chromatography material such as a hollow tubing containing chromatography stationary phases (not shown). One such material suitable for use in this alternate embodiment is Nafion® available from Perma Pure, Toms River, N.J. In view of the foregoing, those in the art will appreciate, the term "chromatography material" as used herein is meant to include chromatography packing material 15 (such as those materials discussed herein), coatings of chromatography material containing chromatography stationary phases (not shown) coated on the wall 9a proximate to the effluent flow channel 9, hollow tubing containing chromatography stationary phases, as well as other stationary phases commonly used in chromatography.

In a preferred embodiment, the electrodes 11 and 13 are flow-through electrodes. By flow-through electrodes, it is meant that the electrodes allow the sample ions and eluant to flow therethrough. The electrodes are preferably made from carbon, platinum, titanium, stainless steel or any other suitable conductive, non-rusting material. The preferred flow-through electrodes are sufficiently porous to allow the sample ions and eluant to flow therethrough, but sufficiently non-porous to physically retain the packing material 15 disposed in the effluent flow channel 9. The most preferred electrodes are made of platinum coated titanium, ruthenium oxide coated titanium, titanium nitride coated titanium, gold, or rhodium with an average pore size of between 0.1 $\mu$m and 100 $\mu$m.

In a preferred aspect of the invention, the flow-through electrodes comprise an annular surface 13a surrounding an inner meshed surface comprising a frit 13b. Preferably, only the annular surface 13a is electroactive; the inner frit surface 13b being made from a non-electroactive material. The annular surface 13a may be made from any of the electroactive materials described above. The inner frit surface 13b is preferably made from PAT™ available from Systec (Minneapolis, Minn.), which is a non-electroactive alloy of TEFLON and PEEK. The foregoing electrode structure provides certain advantages when the eluant comprises an organic substance. Methanol, for example, is converted to formic acid if it comes into contact with a charged surface of the electrode. Thus, if the eluant comprises methanol, it would be converted to formic acid upon contacting the frit surface of the electrode if the frit was made from an electroactive material. Such a result is undesirable in that, among other things, the formic acid by-product could interfere with the analysis. Making the frit surface from a non-electroactive material minimizes the oxidation of methanol, which reduces undesirable by-products when the eluant comprises organic substances such as methanol.

In a most preferred aspect of the invention, the electroactive surfaces of the electrodes 11 and 13 are coated with a Nafion™ coating. Nafion™ is a perfluorinated, hydrophilic, proton conducting ion exchange polymer that exhibits relatively high thermal stability and is not detrimental to the kinetics of electrochemical processes. Further information concerning the Nafion™ coating may be obtained from William T. Callaghan, Manager Technology Commercialization JPL301350 4800 Oak Grove Drive, Pasadena, Calif. 91104. When making such an inquiry refer to NPO19204, Vol. 19, No. 6, NASA Tech. Briefs, p. 66. The foregoing brochure is incorporated herein by reference. The benefits of coating the electrode with Nafion™ is that, as presently understood, the voltage required to obtain a given current may drop by as much as twenty percent when the electrodes 11 and 13 are coated with Nafion™.

The electrodes 11 and 13 are connected to an electrical power source (not shown) via a spade lug (not shown) which is secured in lug receptacles 5a and 5b of female end fitting 2 and male end fitting 3, respectively, by a screw or some other similar means. When the power source (not shown) is turned on, an electric current, caused by ion transport, is established from one of the first or second electrodes to the other across the chromatography packing material 15 when the column is in use. Preferably, the electric current follows along a path that is parallel to fluid flow through the column. Most preferably, the current is a constant current.

As described more fully below, the foregoing column can be used in various apparatuses and methods of electroelution chromatography. The column of the present invention may also be advantageously used as a self-regenerating chemical suppressor. In addition, the column of the present invention can be used in a variety of other applications as well, which are also described herein.

A. Electroelution Elution Chromatography

FIGS. 4–6 illustrate the preferred column of the present invention especially adapted for use in preferred apparatuses and methods for separating, detecting, and analyzing sample ions by electroelution chromatography. As used herein, the term "electroelution chromatography" means eluting sample components from a chromatographic column by electrochemically generating or modifying the mobile phase. In other words, the mobile phase is generated or modified within or prior to entering the column by electrochemical action on the eluant.

FIG. 4 is a schematic view of an apparatus for ion analysis by electroelution chromatography using the preferred column of the present invention. The present embodiment is discussed with respect to the detection of anions in a sample. However, as discussed below, this embodiment may be modified for cation analysis, or for the analysis of anions and cations in the same test sample.

A water-containing eluant source 30 (preferably deionized water) is introduced through a high pressure liquid chromatography (HPLC) pump 32. As those skilled in the art will appreciate, a variety of pumps may be used in this embodiment. However, a metal-free, reciprocating piston pump is preferred, such as the ALLTECH Model 325 pump. The test sample, which contains anions to be detected, is injected through an injector 34, and is routed by the eluant to column 36, which is preferably constructed as depicted in FIGS. 1–3. Again, as those skilled in the art will appreciate, a variety of injectors may be used in the present embodiment. However, metal-free, rotary 6-port injection valves are preferred, such as those available from RHEODYNE (Model No. 9125) or VALCO. The column 36 comprises chromatography packing material. For anion analysis, the column 36 is packed with an anion exchange packing material (not shown). The anion exchange packing material preferably comprises exchangeable hydroxide ions. By "exchangeable," it is meant that the hydroxide ions on the packing material may be displaced (or exchanged with) the sample anions. Suitable anion exchange packing materials comprise particles of primary, secondary, tertiary, or quaternary amino functionalities, either organic or inorganic. Preferred anion exchange packing materials comprise quaternary amino functionality organic or inorganic particles. These anion exchange particles may be packed in the column in either resin form or impregnated in a membrane. Preferably, the anion exchange packing material is in resin form.

The sample anions and eluant are routed through column 36. In column 36, the sample anions displace the exchangeable hydroxide ions on the anion exchange packing material, and are retained in the column 36. Either just before or after the sample anions are retained in column 36, an electric current is generated in column 36 by turning on electrical power supply 38. As those skilled in the art will appreciate, a variety of electrical power supplies may suitably be used in the present embodiment. All that is required for the electrical power supply is that it be capable of providing from about 5–5,000 volts, more preferably from about 28–2,800 volts, and most preferably about 10–1,000 volts to the electrodes in the methods of electroelution chromatography described herein. However, a time-programmable constant-current DC power supply is preferred, such as the LABCONCO Model 3000 Electrophoresis Power Supply. Preferably, the cathode (not shown) of column 36 is located at an upstream end of the column 36, and the anode (not shown) is located at a downstream end of the column 36. Preferably, the electrodes are positioned in the effluent flow channel (not shown) of the column 36. When the water in the eluant contacts the cathode (which is the electrode located at the upstream end of the column 36 for anion analysis), it undergoes electrolysis, and hydroxide ions are generated according to the following reaction:

Cathode: 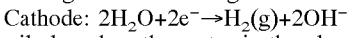
$2H_2O + 2e^- \rightarrow H_2(g) + 2OH^-$

Similarly, when the water in the eluant contacts the anode (which is the electrode located at the downstream end of the column 36 for anion analysis), it undergoes electrolysis, and hydronium ions are generated according to the following reaction:

Anode: 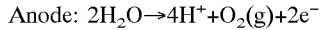
$2H_2O \rightarrow 4H^+ + O_2(g) + 2e^-$

Thus, hydroxide ions and oxygen gas are generated at the upstream end of the column 36, and are routed through the column 36. The hydroxide ions displace the retained sample anions on the anion exchange resin in column 36. The anion exchange resin is thus simultaneously regenerated back to its hydroxide form while the sample anions are eluted. The released sample anions and excess hydroxide ions generated at the upstream located cathode are routed to the downstream end of the column 36 and combine with the hydronium ions generated at the downstream located anode to form the highly conductive acid of the sample anions and relatively non-conductive water, respectively. The effluent from column 36 (e.g., the column effluent), which contains the sample anions in their highly conductive acid form and the relatively non-conductive water, is then routed downstream to a detector 42 in which the sample anions are detected. The detector is preferably a conductivity detector, such as the ALLTECH Model 350 Conductivity Detector. The sample ions detected at the detector may also be quantified by a data system (not shown). The data system is preferably a computer based integrator, such as the HEWLETT-PACKARD General Purpose Chemstation.

Preferably, the effluent from the detector (e.g., detector effluent) is then routed from the detector 42 through a backpressure regulator 44. The backpressure regulator 44 keeps the gaseous $H_2$ and $O_2$ bubbles formed at the cathode and anode, respectively, small enough so that they do not interfere with the detector 42. The backpressure regulator is preferably a spring-energized diaphragm system that maintains constant backpressure on the system regardless of flow rate, such as the ALLTECH backpressure regulator. The detector effluent can then be routed from the backpressure regulator 44 to waste 46. Alternatively, before being routed to the detector 42, the column effluent may be routed through a gas-permeable membrane tube (not shown) positioned between the analytical column 36 and the detector 42. In that way, the gas bubbles generated by the electrolysis of water may be released through the gas permeable membrane to the atmosphere.

In a preferred embodiment, the detector effluent is routed from the back-pressure regulator to an ion exchange bed 45. In anion analysis, the ion exchange bed may be packed with anion exchange packing material (not shown). The anion exchange packing material preferably comprises exchangeable hydroxide ions, and is selected as previously described with respect to column 36. The sample anions replace the exchangeable hydroxide ions on the anion exchange packing material in the ion exchange bed, and the released hydroxide ions combine with the hydronium counterions of the sample anions to form water. The water may then be routed from the ion exchange bed 45 to the water-containing eluant source 30. In this manner, a self-sustaining eluant source is established. Of course, the anion exchange resin in the ion exchange bed 45 will eventually become exhausted, and thus it will need to be periodically replaced or, in the alternative, regenerated according to the methods described herein.

A variety of anions can be separated, detected, and analyzed according to the foregoing method. Examples include chloride ions, nitrate ions, bromide ions, nitrite ions, phosphate ions, sulfate ions, as well as other organic and inorganic anions. FIGS. 5A and 5B are schematic views of column 36 when used in the foregoing method of anion analysis by electroelution chromatography. In FIG. 5A, the sample anions ($X^-$) are retained on the anion exchange packing material 46 that is packed in column 36. Turning to FIG. 5B, when the power source (not shown) is turned on, hydroxide ions generated at the upstream located cathode of the column 36 are routed through the anion exchange packing material and displace the retained sample anions $X^-$. The released sample anions ($X^-$) combine with the hydronium ions generated at the downstream located anode of column 36 to form the highly conductive acid of the sample anions (HX). Additionally, the excess hydroxide ions generated at the upstream located cathode combine with the hydronium ions generated at the downstream located anode to form the relatively low conductive water. Thereafter, the sample anions in their acid form are routed with water from the column 36 to the detector (not shown) where the sample anions are detected.

Based on the foregoing discussion, those skilled in the art will appreciate that the electrodes can be located either outside of or inside the column 36. The only necessary condition with respect to the placement of the electrodes is that at least a portion of the chromatography packing material (anion exchange packing material in the foregoing embodiment) is disposed between the two electrodes, and that fluid flow through the column is from one of the electrodes to the other. Thus, when it is said that the electrode is positioned at an upstream end of the column, it does not necessarily mean that the electrode is actually located in the column. To the contrary, it is simply meant that the electrode is located between the fluid source and the other electrode. Similarly, by the term "downstream end" of the column, it is meant that the electrode is located on the side opposite the fluid source relative to the other electrode. Again, the electrode is not necessarily positioned in the column itself. Thus, fluid flow is always from the "upstream" located electrode to the "downstream" located electrode.

Without being restricted to theory, it is presently believed that the electrical current in column 36 is generated between the two electrodes via ion transport along the chromatography packing material (not shown) in the column 36. However, where the packing material is not capable of ion transport, it is presently believed that ion transport takes place via the mobile phase. This electric current via ion transport surprisingly occurs even when the chromatography packing material and the eluant may not inherently be electrically conductive. Because the electric current is generated by ion transport along the chromatography packing material in the effluent flow channel (not shown) of column 36, the electric current through column 36 is in the same direction as fluid flow through the column 36.

As those skilled in the art will understand, the electrical voltage generated in column 36 must be of sufficient strength for the electrolysis of water to occur. The strength of the current generated in column 36 is directly proportional to the voltage applied at the electrodes, the cross-section area of the electrodes, and the capacity of the packing material in column 36 (e.g. the higher the capacity of the packing material, the lower the resistance is in the column 36). The strength of the current in column 36 is inversely related to the distance between the two electrodes.

The above method and apparatus can also be adapted for the separation, detection, and analysis of sample cations as well. For cation analysis, the column 36 is packed with cation exchange packing material. The cation exchange packing material preferably comprises exchangeable hydronium ions. Preferred cation exchange packing materials include acid functionalized organic and inorganic particles, such as phosphoric acid functionalized organic or inorganic particles, carboxylic acid functionalized organic or inorganic particles, sulfonic acid functionalized organic or inorganic particles, and phenolic acid functionalized organic or inorganic particles. The cation exchange particles may be packed into the column in either resin form or impregnated into a membrane. The most preferred cation exchange packing materials are sulfonic acid functionalized particles. Most preferably, the cation exchange packing material is packed in the column in resin form.

In cation analysis, the apparatus of FIG. 4 is further reconfigured so that the anode (not shown) is positioned at the upstream end of the column 36 and the cathode (not shown) is positioned at the downstream end of the column 36. Thus, when an electric current of sufficient strength is applied, hydronium ions are generated at the upstream located anode 36. The hydronium ions are then routed across the cation exchange packing material and displace the previously retained sample cations in the column 36. The released sample cations and excess hydronium ions generated at the upstream located anode combine with the hydroxide ions generated at the downstream located cathode to form the highly conductive bases of the sample cations and water, respectively. The sample cations, in their basic form, and relatively non-conductive water are then routed to detector 42 where the sample cations are detected. Finally, the detector effluent is preferably routed through ion exchange bed 45, which comprises cation exchange packing material (not shown). The cation exchange packing material preferably comprises exchangeable hydronium ions, and is selected as described above. The sample cations displace the hydronium ions and are retained in the ion exchange bed 45, and the released hydronium ions combine with the hydroxide counterions of the sample cations to form water. The ion exchange bed effluent (which comprises water), is then routed to the water containing eluant source.

With reference back to FIG. 4, in an especially preferred embodiment of the present invention both cation exchange packing material (not shown) and anion exchange packing material (not shown) is packed in column 36. Similarly, ion exchange bed 45 is packed with both cation exchange packing material (not shown) and anion exchange packing material (not shown). Preferably, the cation and anion exchange packing material comprise exchangeable hydronium and hydroxide ions, respectively, and are selected as previously described. In this embodiment, both cations and anions in the same test sample may be analyzed according to the foregoing method of electroelution chromatography. However, this configuration is also preferred even when only cations or only anions are being detected as well.

However, when it is desired to separate both anions and cations in the same sample, a sample comprising anions and cations to be separated is routed through column 36. The sample cations are retained in column 36 on the cation exchange resin and the sample anions are retained in column 36 on the anion exchange resin. The polarity of column 36 is arranged depending on whether cations or anions are to be eluted first. Where it is desired to elute the cations first, the anode (not shown) is located at an upstream end of column 36 and the cathode (not shown) is located at a downstream end of the column 36. The power source 38 is turned on to generate an electric current across the anion exchange resin and cation exchange resin in column 36. Hydronium ions are generated at the upstream located anode by the electrolysis of the water-containing eluant as previously described. Similarly, hydroxide ions are generated at the downstream located cathode as previously described. The hydronium ions are routed through column 36, displacing the retained sample cations and simultaneously regenerating the cation exchange packing material back to its hydronium form. The released sample cations and the excess hydronium ions generated at the upstream located anode combine with hydroxide ions generated at the downstream located cathode to form the highly conductive bases of the sample cations and the relatively non-conductive water, respectively.

The sample cations (in their base form) and water are then routed to detector 42 where the sample cations are detected. The detector effluent may then be routed to the ion exchange bed 45 where the sample cations are retained by displacing the hydronium ions on the cation exchange packing material in the ion exchange bed 45. The hydronium ions displaced from the cation exchange packing material combine with the hydroxide counterions of the sample cations to form water, which may then be routed to the water-containing eluant source 30.

After the sample cations have been detected, the polarity of column 36 is reversed, so that the cathode (not shown) is located at an upstream end of column 36 and the anode (not shown) is located at a downstream end of the column 36. Hydroxide ions are generated at the upstream located cathode and hydronium ions are generated at the downstream located anode by electrolysis of the water-containing eluant as previously described. The hydroxide ions are routed through column 36, displacing the retained sample anions and simultaneously regenerating the anion exchange packing material back to its hydroxide form. The released sample anions and the excess hydroxide ions generated at the upstream located cathode combine with the hydronium ions generated at the downstream located anode to form the highly conductive acids of the sample anions and the relatively non-conductive water, respectively.

The sample anions (in their acid form) and water are routed to the detector 42 where the sample anions are detected. The detector effluent may then be routed to the ion exchange bed 45 where the sample anions are retained by displacing the hydroxide ions on the anion exchange packing material in the ion exchange bed 45. The displaced hydroxide ions then combine with the hydronium counterions of the sample anion to form water, which may then be routed to the water-containing eluant source 30.

In another embodiment of the present invention, two columns as illustrated in FIG. 1 can be arranged in series for use in methods of detecting cations and anions in the same test sample. With reference to FIG. 6, a water-containing eluant source 30 (again, preferably deionized water) is introduced through a high pressure liquid chromatography (HPLC) pump 32. A test sample containing both anions and cations to be detected is injected through an injector 34, and is carried by the eluant to a first column 36 of the present invention, which is packed with anion exchange packing material (not shown). The anion exchange packing material preferably comprises exchangeable hydroxide ions, and is selected as previously described.

The sample anions displace the hydroxide ions on the anion exchange resin and are retained in the first column 36. The first column effluent, which contains the sample cations and displaced hydroxide ions, is routed to a second column 136. Column 136 is packed with cation exchange packing material preferably comprising exchangeable hydronium ions, and is selected as previously described. The sample cations displace the hydronium ions on the cation exchange packing material and are retained in the column 136. The released hydronium ions neutralize the hydroxide ions in the first column effluent to form water. The water is then preferably routed through the detector 42 (giving no signal), through an ion exchange bed 46, through valve 48 and back to the eluant source 30.

An electric current sufficient to electrolyze water is then generated in column 36 across the anion exchange packing material by turning on electric power supply 38. The cathode (not shown) of the column 36 is located at an upstream end and the anode (not shown) is located at a downstream end of the column 36. The water-containing eluant undergoes electrolysis at the upstream located cathode thereby generating hydroxide ions and hydrogen gas as previously described. The hydroxide ions generated at the upstream located cathode are routed through the column 36 and displace the retained sample anions on the anion exchange packing material thereby eluting the sample anions from column 36.

At the downstream located anode of the column 36, hydronium ions and oxygen gas are generated as previously described by the electrolysis of the water-containing eluant. The released sample anions from column 36 and the excess hydroxide ions generated at the upstream located anode of the column 36 combine with the hydronium ions generated at the downstream located cathode of the column 36, to form the highly conductive acids of the sample anions and relatively non-conductive water, respectively.

The acids of the sample anions and water from column 36 are routed through column 136 unretained to detector 42, in which the sample anions are detected and quantified by a data system 43. The bubbles formed by the hydrogen gas and oxygen gas generated at the cathode and anode, respectively, of the column 36 are kept small enough by back pressure regulator 44 so that they do not interfere with the detector 42.

The detector effluent is then preferably routed from the detector 42 through back pressure regulator 44 to an ion exchange bed 46 comprising ion exchange packing material having exchangeable hydronium and exchangeable hydroxide ions. The ion exchange bed is preferably of high-purity such as those used to produce deionized water. The sample anions displace the hydroxide ions and are retained in the ion exchange bed 46. The displaced hydroxide ions neutralize the resulting hydronium counterions of the sample anions to form water, which is preferably routed through valve 48 back to the eluant source 30.

Once the sample anions have been detected, an electric current sufficient to electrolyze water is then generated in column 136 across the cation exchange packing material by turning on electric power source 138. The anode (not shown) is positioned at an upstream end of the column 136 and the cathode (not shown) is located at a downstream end of the column 136. The water containing eluant undergoes electrolysis at the upstream located anode of the column 136 thereby generating hydronium ions. The hydronium ions are then routed through the column 136 and displace the previously retained sample cations on the cation exchange resin thereby eluting the sample cations from column 136.

At the downstream located cathode (not shown) of column 136, hydroxide ions and hydrogen gas are generated as previously described by the electrolysis of the water-containing eluant. The released sample cations and the excess hydronium ions generated at the upstream located cathode of the column 136 combine with the hydroxide ions generated at the downstream located anode of the column 136, to form the highly conductive bases of the sample cations and relatively non-conductive water, respectively.

The sample cations (in their base form) and water are then routed from column 136 to detector 42, in which the sample cations are detected and quantified by data system 43. Again, the bubbles formed by the hydrogen gas and oxygen gas generated at the cathode and anode, respectively, of the column 136 are kept small enough by the backpressure regulator 44 so that they do not interfere with the detector 42.

The detector effluent is then preferably routed from the detector 42 through backpressure regulator 44 to the ion exchange bed 46. The sample cations displace the exchangeable hydronium ions in the ion exchange bed 46 and are retained therein. The displaced hydronium ions neutralize the hydroxide counterions of the sample cations to form water, which is preferably routed through valve 48 back to eluant source 30.

FIG. 7 is a chromatogram of a test sample containing both anions and cations separated pursuant to the foregoing method and apparatus of the present invention. The first series of peaks represent the sample anions that are eluted when power is applied and an electric current is generated across the anion exchange packing material in column 36. The second series of peaks represent the sample cations that are eluted and detected when power is applied and an electric current is generated across the cation exchange packing material in column 136.

As those skilled in the art will recognize, the foregoing apparatus and method can be easily reconfigured so that the column 36 is packed with cation exchange packing material and the anode is located at an upstream end and the cathode is located at a downstream end of the column 36, and column 136 is packed with anion exchange packing material and the cathode is located at a upstream end and the anode is located at a downstream end of the column 136.

The foregoing methods and apparatuses provide many advantages. For example, the strength of the current applied in the columns 36 and 136 will determine the concentration of hydroxide and hydronium ions generated in these columns. The higher the current, the greater the concentration of hydroxide or hydronium ions and the easier and quicker the sample anions and cations will be eluted. Thus, gradients are therefore possible through time-based current programming in the anion and cation columns. Moreover, the foregoing method can be configured as a closed loop system. Additionally, simultaneous cation and anion analysis is possible with high sensitivity and low background noise. Moreover, water dips, and unretained counter-cation peaks, and unretained counter-anion peaks often present in traditional ion chromatography methods may be reduced and even eliminated.

The methods and apparatuses previously described can also be used in methods and apparatuses for the electroelution of proteins, as well as any other test sample whose affinity for chromatographic packing material is affected by Ph changes and/or ionic strength changes. Proteins and many other test samples retain on affinity stationary phases by biological recognition, on reversed phases by hydrophobic interactions, on ion-exchange or chelation packing materials by charge interactions, by size on size exclusion packing materials, by hydrophobic interactions on hydrophobic packing materials, and by normal phase interactions on normal phase packing materials. All of these retention mechanisms may be mediated by ionic strength and/or Ph.

By using the electrolysis of water as discussed in the foregoing embodiment, the hydrogen and hydroxide ion concentration in the column illustrated in FIG. 1 can be controlled, thereby permitting the control of the Ph and ionic strength inside the column. Thus, by packing the chromatography column of the present invention with an ion-exchange, affinity stationary phase, reversed phase, size exclusion, chelating, hydrophobic, or normal phase chromatography packing material, proteins or other samples can be retained when no power is applied to the column. However, when power is applied to generate hydronium ions (decrease Ph) or hydroxide ions (increase Ph) within the column, the resulting ionic strength and Ph change may be used to elute the retained protein (or other samples) from the column. Thus, the column of the present invention can be used to separate and purify a wide range of compounds on both an analytical and preparative scale.

Suitable packing materials for use in the foregoing embodiment include Protein A affinity packing material as the affinity phase packing material; C-18 reversed phase packing material as the reversed phase packing material; Chelex-100 from Bio-Rad in the chelating packing material; ALLTECH Macrosphere GPC as the size exclusion packing material; SYNCHROM SynChropak HIC as the hydrophobic packing material; and ALLTECH Alitima Silica as the normal phase packing material.

Additionally, as discussed below, the column of the present invention can also be used as a self-regenerating solid phase chemical suppressor in various apparatuses and chromatography methods.

B. Electrochemically Regenerated Solid Phase Chemical Suppressor

1. System Configurations for Anion Analysis

FIGS. 8A–8D are schematic views of various preferred apparatus configurations for a preferred method of ion analysis using the column illustrated in FIG. 1 as a self-regenerating solid phase chemical suppressor. With reference to FIG. 8A, an eluant source 202 is in fluid connection with a pump 204. Downstream from the pump 204 is an injector 206 where a test sample can be added to the system. Located downstream from the injector 206 is an analytical (or chromatography) column 208 where separation of the ions in the test sample occurs. In anion analysis, a low-capacity anion exchange column is preferably used. For cation analysis, a low-capacity cation exchange column is preferably used.

Located downstream from, and in fluid connection with, the analytical column 208, is a 10-port switching valve 210. The switching valve is preferably of the metal-free rotary type. In connection with the 10-port switching valve 210 are two columns, 212 and 214, respectively, as illustrated in FIG. 1. Connected to columns 212 and 214 are electrical power sources 216a and 216b, respectively. One power source connected to both columns 212 and 214 may be used as well. This embodiment generally requires lower voltage than the foregoing methods of electroelution chromatography because the capacity of the chromatography packing materials in this embodiment is greater (e.g. lower resistance), and thus lower voltages are capable of generating a current sufficient for the electrolysis of water. A preferred power source is the KENWOOD PR 36-1.2 power supply. When the column illustrated in FIG. 1 is used as a suppressor, the power source should be capable of delivering about 1–100 volts to the electrodes, more preferably about 10–90 volts, and most preferably about 3–15 volts. Finally, a conductivity detector 218 is connected with 10-port switching valve 210. As described in more detail below, the column illustrated in FIG. 1 is adapted for use as a self-regenerating solid phase chemical suppressor in the foregoing configuration.

Still with reference to FIG. 8A, an aqueous eluant source 202 introduces eluant through a HPLC pump 204. A test sample containing anions to be detected is injected through injector 206, and is routed by the eluant to analytical (or chromatography) column 208. In the present embodiment (e.g., anion analysis) the eluant may comprise solutions of sodium carbonate, sodium bicarbonate, sodium hydroxide or some other base that is converted to a weak acid by counterion exchange with hydronium ions. The most preferred eluant for anion analysis are solutions of sodium hydroxide.

The analytical column 208 is preferably packed with anion exchange packing material (not shown). Suitable anion exchange packing materials comprise particles of primary, secondary, tertiary, or quaternary amino functionalities, either organic or inorganic. The preferred anion exchange packing materials comprise quaternary amino functionality organic or inorganic particles. These anion exchange particles may either be packed into the column in resin form or impregnated into a membrane. Preferably, the packing material is in resin form.

Different anions in the test sample have differing affinities for the anion exchange packing material in the analytical column 208. The stronger the affinity of a particular type of anion for the packing material in the analytical column 208, the longer that type of anion will be retained in the column 208. Conversely, the weaker the affinity of a particular type of anion for the packing material in the analytical column 208, the shorter that particular type of anion will be retained in the column 208. Thus, because different anions have different affinities for the packing material in column 208, the sample anions are eluted at different speeds from the column 208 and are therefore separated or resolved.

The effluent from analytical column 208 (hereinafter referred to as "chromatography effluent") is routed from the column 208 through 10-port switching valve 210 to column 212. In this embodiment, the column 212 is adapted for use as a suppressor in a method of anion analysis. The column 212 is packed with cation exchange packing material (not shown). Preferred cation exchange packing materials include acid functionalized organic or inorganic particles, such as phosphoric acid functionalized organic or inorganic particles, carboxylic acid functionalized organic or inorganic particles, phenolic acid functionalized organic or inorganic particles, and sulfonic acid functionalized inorganic or organic particles. The cation exchange particles may either be packed into the column in resin form or impregnated into a membrane. The most preferred cation exchange packing materials are sulfonic acid functionalized inorganic or organic particles in resin form.

Two ion-exchange reactions take place in the suppressor 212:
1. Eluant:
   (where the eluant is sodium hydroxide and the cation exchange packing material comprises sulfonic acid functionalized particles):
   $NaOH+Resin-SO_3^-H^+ \rightarrow Resin-SO_3^-Na^+ + H_2O$
2. Analyte:
   $NaX+Resin-SO_3^-H^+ \rightarrow Resin-SO_3^-Na^+ + HX$
   (where X=anions such as Cl, $NO_2$, Br etc.)

The sodium ions in the high conductivity eluant are removed by ion exchange with the hydronium ions present on the cation exchange packing material in the column 212. The high conductivity sodium hydroxide eluant is thus converted to the relatively non-conductive water (the sample counterions are also suppressed by ion exchange with hydronium ions on the cation exchange packing material). This, of course, reduces the background noise from the eluant (and sample counterions) when the sample anions are ultimately detected in the detector 218. The sample anions are converted into their highly conductive acid form by exchanging their counterions with hydronium ions on the cation exchange packing material in the column 212. As can be ascertained from the above reactions, the eluant in anion analysis can be any salt solution that forms a weakly conductive acid in the suppressor 212. Examples of suitable eluants include aqueous solutions of sodium hydroxide, sodium carbonate/bicarbonate, and sodium tetraborate. The eluant must further comprise water, however, to feed the electrolysis in the methods of the invention.

After the eluant has been converted to its weak acid and the sample anions to their highly conductive acids in the column 212, the suppressor effluent is routed through the 10-port switching valve 210 to detector 218 where the sample anions are detected. Data from the detection of the sample anions is preferably recorded on a chart, graph, an integrator, a computer or other recording means (not shown). The effluent from the detector 218 (hereinafter referred to as "detector effluent") is then routed through 10-port switching valve 210, and column 214 to waste.

When the cation exchange packing material in suppressor 212 is exhausted (e.g., completely converted from the hydrogen to sodium form), a sharp increase in the conductance of the suppressor effluent is observed. Before this happens, the 10-port switching valve 210 is switched to the configuration depicted in FIG. 8B. While using the column 214 to suppress the chromatography effluent in the same manner as previously described with respect to column 212, the detector effluent is recycled back through 10-port switching valve 210 to the exhausted suppressor 212 to regenerate it as follows.

A power source 216a is turned on thereby generating an electric current sufficient for the electrolysis of water across the exhausted cation exchange packing material in suppressor 212. Suppressor 212 is configured so that the anode (not shown) is positioned at the upstream end and the cathode (not shown) is positioned at the downstream end of the suppressor 212. The detector effluent (which contains water) undergoes electrolysis at the upstream located anode of suppressor 212 as previously described:

$2H_2O \rightarrow 4H^+ + O_2 + 4e^-$

Hydronium ions and oxygen gas are thus generated at the upstream anode of suppressor 212. Since the detector effluent is flowing from the anode side to the cathode side of the suppressor 212, the hydronium ions are routed across the exhausted cation exchange packing material in suppressor 212 converting it back to the hydrogen form according to the following reaction:

$Resin-SO_3^-Na^+ + H^+ \rightarrow Resin-SO_3^-H^+ + Na^+$

The oxygen gas and displaced sodium ions (and sample counterions) from suppressor 212 are then routed through 10-port switching valve 210 to waste.

At the downstream located cathode of suppressor 212, water undergoes electrolysis as previously described:

$2H_2O + 2e^- \rightarrow H_2 + 2OH^-$

Hydroxide ions and hydrogen gas are thus generated at the downstream end of suppressor 212. The hydroxide ions and hydrogen gas generated in suppressor 212 are routed through 10-port switching valve 10 to waste.

Alternately, the systems waste products may be recycled. As can be appreciated from the above chemical reactions, the regeneration process liberates exactly the same mass of eluant ions consumed during the suppression process. Because the process is quantitative, routing the waste products from switching valve 10 back to eluant source 2 on a continuous basis will result in continuous reconstitution of the original eluant (in this embodiment sodium hydroxide), eliminating chemical waste.

Power source 216a is left on long enough to regenerate the cation exchange packing material in suppressor 212. Once the suppressor 212 is regenerated, the power source is turned off. The detector effluent is still preferably routed through the suppressor 212, however, for a time sufficient to purge any remaining gas bubbles and electrolysis products in suppressor 212, and to equilibrate the column. Once the suppressor 212 is regenerated and equilibrated, it is ready for use as the "active" suppressor when suppressor 214 becomes exhausted. Once suppressor 212 is ready to go back on line, the analytical column effluent is re-routed to suppressor 212 and suppressor 214 is regenerated in the same manner as previously described with respect to suppressor 212.

The foregoing arrangement allows endless cycling between the two suppressors 212 and 214 for continuous instrument operation without interruption or suppressor replacement. Preferably, when the eluant comprises an organic such as methanol, after regeneration the eluant is allowed to pass through the suppressor for a time (usually about 5 minutes) sufficient to wash unwanted components that may remain in the suppressor after regeneration. Once these unwanted by-products are purged from the suppressor, the sample to be analyzed may then be injected into the system. The system is easily automated using automatic valves and power supplies to provide unattended operation for extended periods.

Figure 23A:
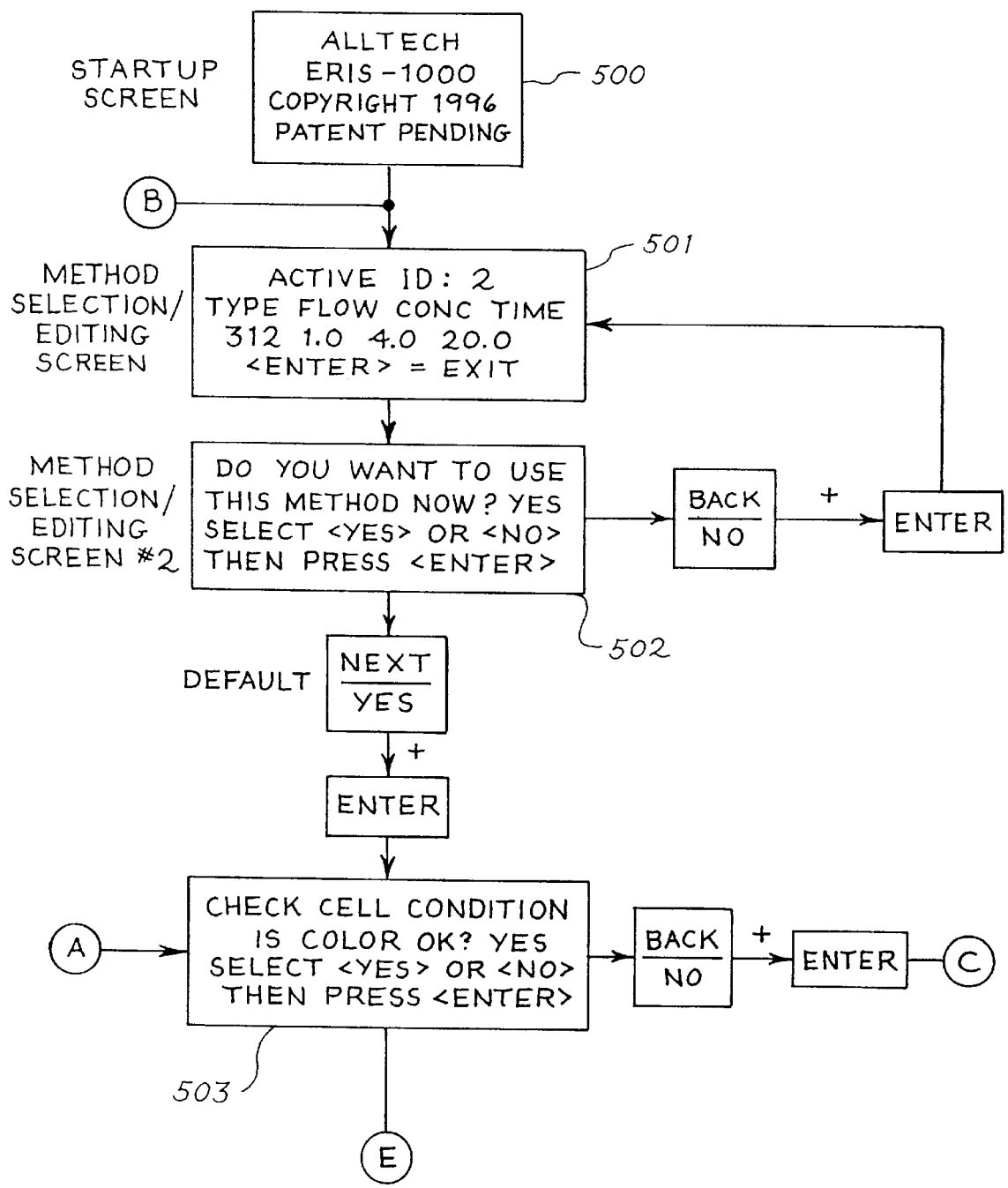
FIGS. 23(a)–(c) is a flowchart for the computer program used in one preferred aspect of the invention.
Figure 23A:
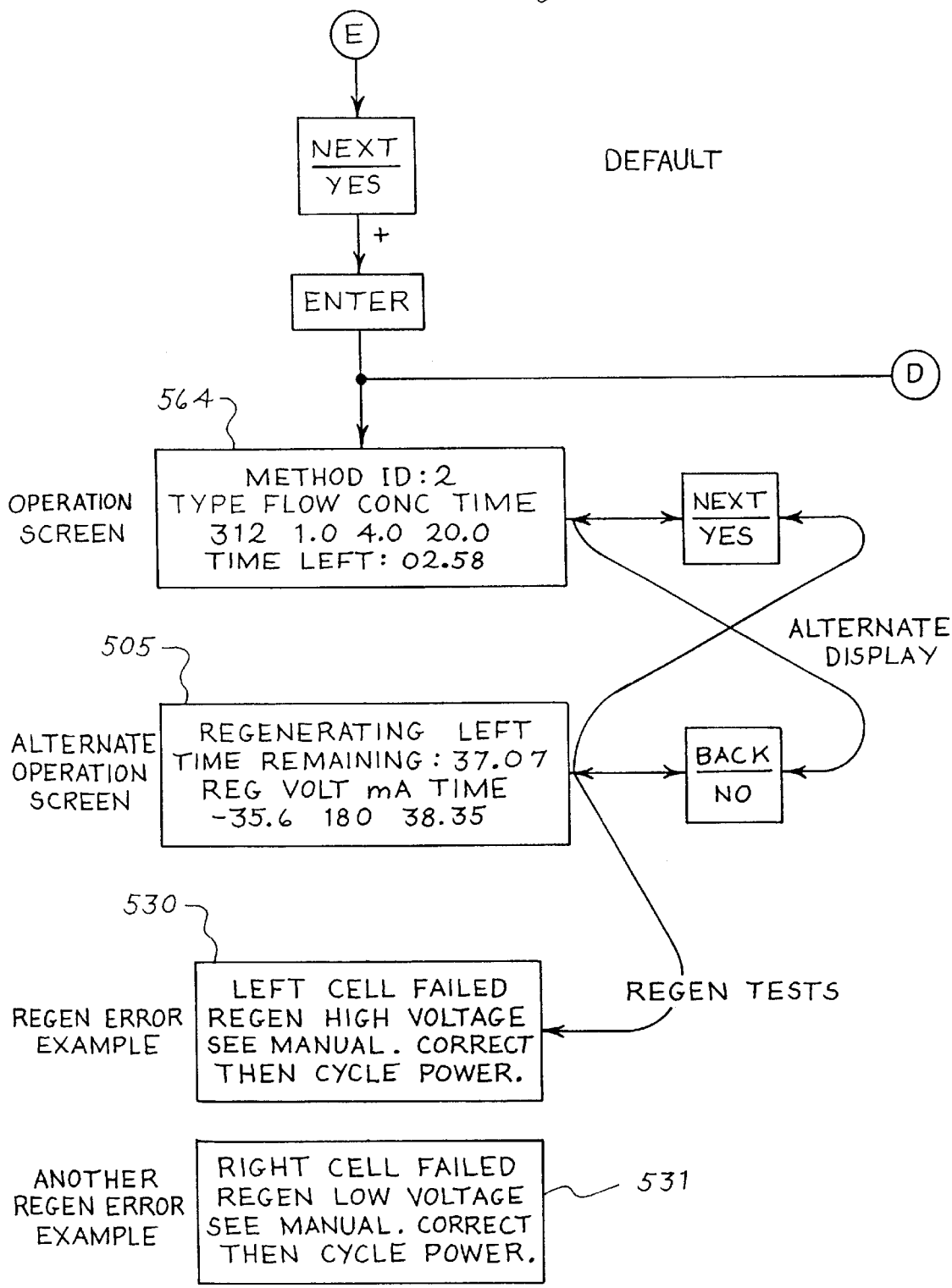
Figure 23B:
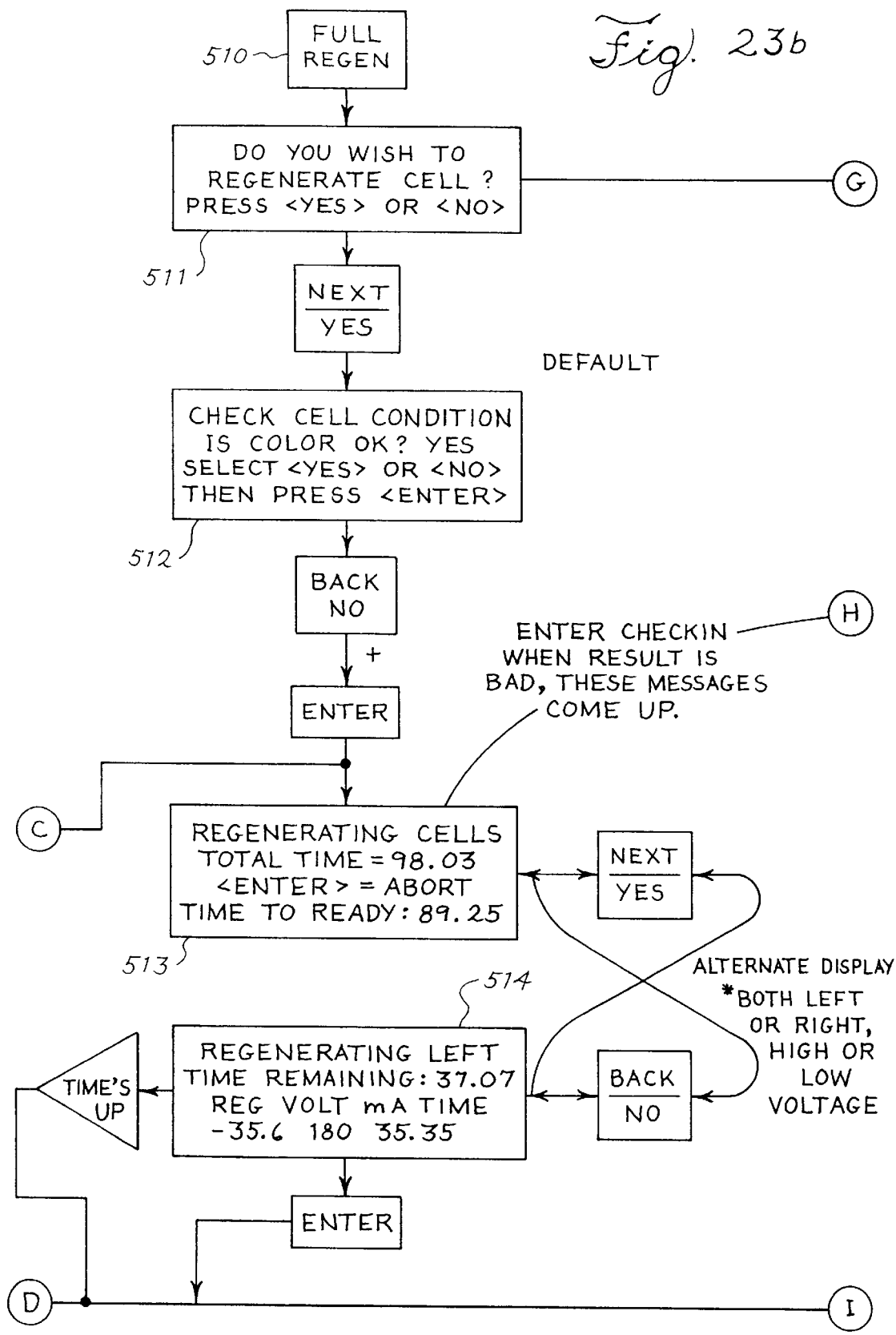
Figure 23B:
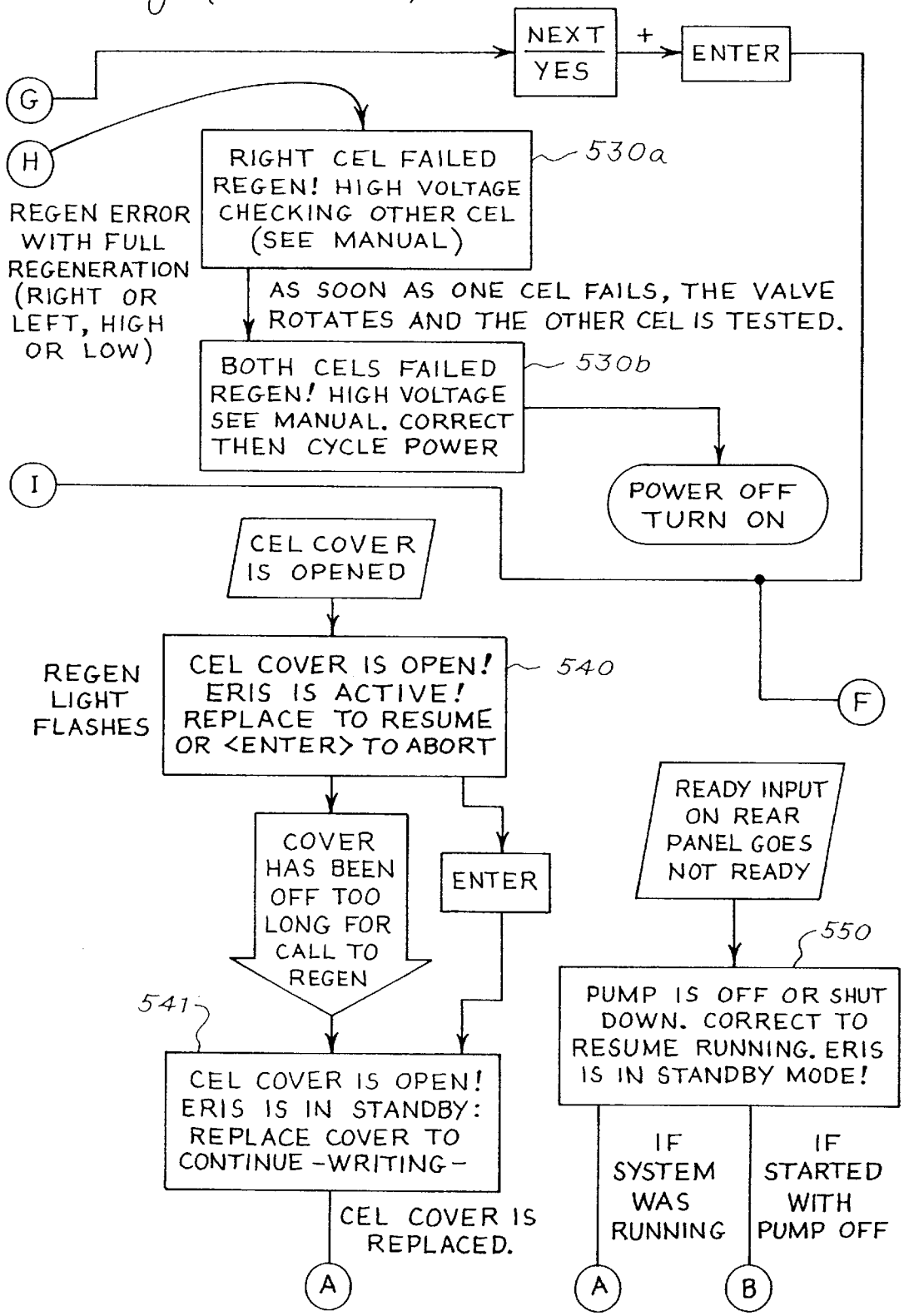
Figure 23C:
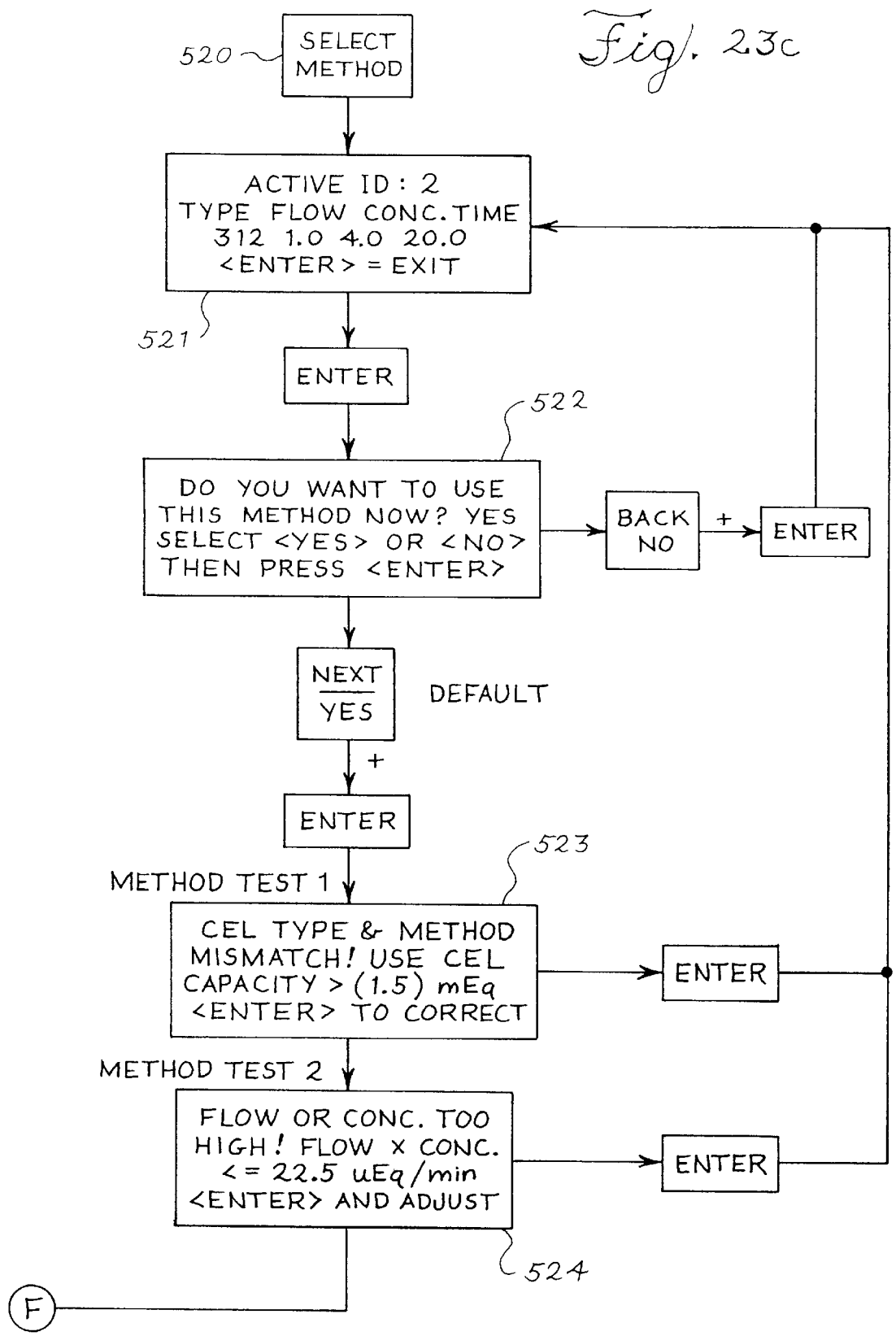

In one aspect of the invention, a computer program is used to implement and automate the switching between suppressors. One presently preferred flowchart providing an overview of such computer program and its functions is provided in FIGS. 23(a)–(c). A computer program following the procedures and functions shown in FIGS. 23(a)–(c) is provided in the Appendix. The presently preferred computer program is written in the Forth computer language although, as those skilled in the art will appreciate, the flowchart shown in FIGS. 23(a)–(c) can be implemented in any computer language without departing from the spirit and scope of the invention.

In a presently preferred embodiment, the above-referenced software will be used to run a self-contained suppressor system comprising two solid-phase electrochemical suppressors packed with ion exchange resin, a two position electrically actuated 10-port switching valve, a constant current power supply and a microprocessor for executing the computer software attached in Appendix A. These components are preferably housed together in one housing. A suitable microprocessor is the MOTOROLA 8-bit microprocessor (Motorola Part No. 68HCP11 A1 FN) operating with a 4 mHz crystal, 32 K×8 EPROM, National Part No. 27C256 and 8K×8 RAM, MOSEL Model Part No. MS 6264C-80PC.

With respect to this suppressor system, the mobile phase from the separator (or analytical) column flows through one suppressor at a time. While one suppressor is being used, the other is electrochemically regenerated and equilibrated. The valve switches between suppressors after each sample injection, providing a fresh suppressor cell for each analysis. Preferably, the suppressors will be of relatively small volume to avoid problems such as band broadening, Donnan exclusion, and the oxidation of nitrite to nitrate associated with conventional packed-bed suppressors. The suppressors are preferably either 7.0 by 7.5 mm or 14×7.5 mm in internal diameter. Finally, the operator interface on the front panel of the suppressor unit has a series of buttons or keys (which are discussed below) for easy operation of the unit by lab personnel.

The ion exchange resin in the suppressors is preferably visible when the suppressors are housed in the suppressor unit so that suppressor status may be monitored at all times. This is accomplished by housing the suppressors in a compartment having a transparent cover on a front panel or operator interface of the unit. The suppressor status may be indicated by coating the ion-exchange resin with an inert dye, which changes color as the suppressor resin becomes exhausted. For anion analysis, the suppressors are packed with cation exchange resin in the hydrogen form, and the resin is coated with an inert dye comprising quinaldine red. The unexhausted resin thus has a gold color, which changes to magenta during suppression as the hydrogen ions on the resin are replaced by the mobile phase and sample counterions. For cation analysis, the suppressors are packed with anion exchange resin in the hydroxide form, and the resin is coated with an inert dye comprising thymolphthalein. The unexhausted resin thus has a blue color, which changes to beige during suppression as the hydroxide ions on the resin are replaced by the mobile phase and sample counterions.

A brochure for a self-contained suppressor unit according to one preferred aspect of the invention is attached in the Appendix. This brochure (e.g. Alltech, Bulletin #334) refers to Alltech's ERIS™ 1000 Autosuppressor, and is incorporated herein by reference. The software presently contemplated for use with the Alltech ERIS™ 1000 Autosuppressor is attached in the Appendix and a flowchart providing an overview of this software is at FIGS. 23(a)–(c). Among other things, the software automatically coordinates suppression and regeneration based on data inputted by the operator and based on signals received from other external devices in the chromatography system. The software also generates messages on a system display concerning operational parameters, regeneration parameters and status and system errors. The system display is preferably a four line alpha numeric display and is positioned on the operator interface of the suppressor unit. A copy of the most current draft of the Operator's Manual for the Alltech ERIS™ 1000 Autosuppressor is attached in the Appendix. This Operator's Manual is also incorporated herein by reference.

With reference to FIGS. 23(a)–(c), Step 500 is the beginning of the software and depicts the startup screen when the suppressor unit is powered-up. Program flow then proceeds to step 501. At step 501, a message is generated on the system display indicating the "Active" method, which is the method presently inputted in the system for the next sample injection. The "Active ID" has a one or two digit number having associated pre-assigned parameter values for a given method. The system may store up to twelve different "Active ID" numbers, each having pre-assigned method parameters. The system comes with two preassigned "Active ID" "numbers," EPA-A and EPA-B (EPA Method 300, parts A and B, respectively). If selected, "EPA-A" or "EPA-B" will appear on the system display as the "Active ID". Additionally, ten "Active ID" numbers (e.g. 1–10) may be inputted into the system wherein each number has its own unique operating parameters. In addition to calling up any one of the twelve Active ID numbers having pre-assigned parameters, new operating parameters may also be inputted into the system for a particular sample run by depressing the "Select Method" button on the operator interface. The procedure for inputting new operating parameters will be discussed in more detail below.

Referring back to the message at step 501, the three digit number underneath the "Type" heading provides information concerning the type and capacity of the individual suppressors. In step 501, the three numbers corresponding to the "type" heading are "312." The first digit (e.g., "3") refers to the type of sample analysis (i.e., either anion or cation analysis), and, thus, the type of suppressor in the system. The system will automatically set the polarity of the electrodes based on this entry. For example, the number "3" signifies anion analysis. This tells the system to configure the electrode positioned at the detector effluent end of the suppressor as the anode. Conversely, if the number "2" were entered in place of "3" the system would automatically reverse the polarity of the electrodes making the electrode positioned at the detector effluent end of the suppressor the cathode. The next two digits under the "Type" heading (e.g., "12") refer to the capacity of the individual suppressors in milliequivalents (meq.) times 10. Thus, the screen at step 501 indicates a suppressor for anion analysis having a capacity of 1.2 milliequivalents. In a preferred embodiment, the suppressors themselves will have a label or some other attached means for displaying a three digit number to correspond to the "Type" number discussed above. Thus, for example, a suppressor bearing the number "312" is for anion analysis and has a capacity of 1.2 milliequilvalents. As those skilled in the art will appreciate, the two suppressors should have the same capacity in this embodiment.

Still with respect to the message generated at step 501, the "Flow" heading refers to the flowrate in mL/min. for the analysis. The screen at step 501 indicates a flowrate of 1.0 mL/min. The "Conc." heading in the message generated at step 501 refers to the concentration of the mobile phase in milliequivalents/Liter (meq./L). For anion analysis, the meq./L of cations in the mobile phase is indicated. Conversely, for cation analysis, the meq./L of anions in the mobile phase is indicated. Because the message at step 501 indicates anion analysis, the concentration of 4.0 meq./L refers to the concentration of cations in the mobile phase. Finally, the "Time" heading in the message generated at step 501, refers to the total run time for the analysis to a tenth of a minute.

To exit the screen at step 501 and proceed to the next screen the operator merely depresses an "Enter" button on the operator interface and program flow will proceed to step 502. In step 502 a message is generated on the system display asking whether the operator wishes to proceed with the method having the parameters indicated at step 501. If yes, the operator will then depress a "Next/Yes" button and then the "Enter" button on the operator interface and program flow proceeds to step 503. If the answer is "No," then the operator may depress a "Back/No" button and then the "Enter" button on the operator interface to recall the screen at step 501. The operator may then edit the parameters indicated at step 501 by depressing a "Select Method" button key on the operator interface. Details concerning inputting new method parameters are discussed in further detail below.

Referring back to step 503, a message is generated on the system display requesting that the suppressor ("Cell") color be checked. If the color condition is "O.K.," that is, if the color indicates that the suppressors are in a condition to accept a sample injection, the operator may depress the "Next/Yes" and then the "Enter" buttons on the operator interface and the program flow proceeds to step 504. The system is now ready to receive a sample injection.

The system is programmed to switch between suppressors after each sample injection. Samples may be injected manually or automatically. For manual injection, an "Inject/Start" button is provided on the user interface, which should be depressed simultaneously with the introduction of the sample. Additionally, pins located on the rear panel of the operator interface are designed to accept a sample injection signal from an external device such as an autosampler or a manual injection valve equipped with a position sensing switch. While waiting for a sample injection, the system will cycle the mobile phase between the two suppressor cells. Once the total analysis time elapses for the particular method inputted into the system, the system will automatically direct the mobile phase to a fresh suppressor and will begin counting down the total analysis time. Upon receiving an injection signal, the system resets the total analysis time, but continues directing column effluent to the active suppressor (because the new suppressor has not yet "seen" an injection). The valve will automatically rotate to the other suppressor the next time the system receives an injection signal or when the analysis time has elapsed, whichever comes first. The system software thus ensures that only one sample injection is allowed to flow through the suppressor between regeneration cycles regardless of when the sample is injected.

Referring back to step 504, a message is generated on the system display pertaining to the "Method ID". The Method ID indicates the current operating parameters (e.g., cell type, flowrate, eluant concentration and analysis run time), and the time remaining until the sample analysis is complete. While one suppressor is in the suppressing mode the other suppressor is regenerated by the electrolysis of the detector effluent. By depressing the "Next/Yes" button on the operator interface, a message is generated at step 505. This screen shows the total regeneration (or flushing) time in minutes and seconds (min.:sec), the remaining regeneration time (or flushing) time (min.:sec.), how much current is applied to the electrodes in the suppressor being regenerated, and the voltage across the suppressor being regenerated.

Based on the flowrate, mobile phase concentration and total run time entered for the particular method, the system automatically calculates the amount of current required to completely regenerate the suppressor within 40% of the run time. A negative voltage indicates that the suppressor being regenerated is for anion analysis. A positive voltage indicates that the cell being regenerated is for cation analysis. The message at step 505 indicates that the left suppressor is being regenerated while the right suppressor is in the active or suppressing mode. The operator may toggle between the screens displayed in steps 504 and 505, respectively, by depressing the "Next/Yes" and "Back/No" buttons on the operator interface. The current is applied to the suppressor undergoing regeneration just long enough to regenerate the suppressor (as calculated by the system based on the method parameters) and then the current is automatically shut off when regeneration is complete. However, detector effluent continues to flow through the regenerated suppressor to purge any remaining gas bubbles and other electrolysis by-products.

The operator interface also has a cell (e.g., suppressor) status display. This display indicates the cell is "IN USE", and whether the other cell is either being "REGEN" (e.g., regenerated) or is "READY" (i.e., regeneration has been completed). The suppressors are positioned in a compartment on the operator interface and the compartment has a transparent door so that the suppressors are visible to the operator. The cell status display is positioned above the compartment housing the suppressors and comprises a separate display for each of the "LEFT" and "RIGHT" suppressors, respectively. Thus, for example, if the LEFT suppressor is on line (i.e., in the active or suppressing mode), the cell status display for the "LEFT" suppressor will display an "IN USE" message. While the LEFT suppressor is in use, the cell display for the "RIGHT" suppressor will display either a "REGEN" or a "READY" message, depending on whether the "RIGHT" suppressor is being regenerated or regeneration has been completed, respectively.

If for any reason the operator desires to regenerate both of the suppressors in the system, the operator may depress a "FULL REGEN" (e.g. Full Regeneration) button on the operator interface. Program flow then proceeds to step 511. The "FULL REGEN" button may be depressed at anytime during the display of the "Method ID" screen. A message is generated on the system display at step 511 asking for confirmation that suppressor regeneration is desired. By depressing the "Next/Yes" button on the operator interface, program flow then proceeds to step 512 where a message is generated on the system display requesting the operator to "Check Cell Condition". If the color of the resin in the suppressors indicates that the suppressors are in the unexhausted form, the operator may depress the "Next/Yes" and then the "Enter" buttons on the operator interface and program flow proceeds to step 504. In which case, the system is ready to receive a sample injection. Conversely, if the resin color indicates that the suppressors are exhausted, and thus regeneration is desirable, the operator may depress the "Back/No" and then the "Enter" buttons on the operator interface and program flow proceeds to step 513.

The system then begins to regenerate both of the suppressors, and a message is generated on the system display at step 513 giving the total time (min.:sec.) required to regenerate both suppressors and the remaining time (min.:sec.) until both suppressors are regenerated. Again, the time to regenerate the suppressors is calculated by the system based on the operating or method parameters inputted by the operator. Only one suppressor is regenerated at a time, and specific information concerning the suppressor being regenerated may be obtained by depressing the "Next/Yes" button on the operator interface at Step 513 and program flow will proceed to step 514. At step 514 a message similar to that generated at step 505 is generated on the system display. This message reports on the status of the suppressor undergoing regeneration at that moment, which in step 514 is the left suppressor. The operator may toggle between screens 513 and 514 by depressing the "Next/Yes" and "Back/No" buttons on the operator interface. Once both the suppressors are regenerated, program flow then proceeds to step 504 and the system is ready to accept a sample injection. Also, the program allows for aborting regeneration of the suppressors at any time by simply depressing the "Enter" button on the operator interface at step 513. This will abort the regeneration sequence and program flow will proceed to step 503.

Method parameters may be entered or changed at the beginning of the software, or at any other time by simply depressing the "Select Method" (Step 520) button on the operator interface. Program flow then proceeds to step 521. At step 521, a message is generated on the system display indicating the method parameters. By depressing the "Next/Yes" and "Back/No" buttons on the operator interface the operator may scroll through the parameters—Type, Flow, Conc. and Time. Arrow buttons on the operator interface are used to increase or decrease the numerical values for each of these parameters. Once the desired operating parameters are set, the "Enter" button on the operator interface is depressed and program flow then proceeds to step 522. A message is generated on the system display at step 522. If the operator wishes to proceed with the method parameters selected at step 521, the "Next/Yes" and then the "Enter" buttons are depressed at step 522 and program flow proceeds to step 504 and the system is ready to accept a sample injection. Conversely, if the operator does not wish to proceed with the parameters selected in step 521, the "Back/No" and then the "Enter" buttons are depressed on the operator interface at step 522 and program flow proceeds back to step 521.

When selecting method parameters at step 521, certain considerations must be taken into account. When entering the three digit number for "Type" of method, the type of analysis (i.e., whether cation or anion analysis) and the capacity (in meq./L) of the suppressors in the system must be entered. When entering the flow rate (e.g., "Flow"), the operator must match the flow rate with that of the HPLC pump in the chromatography system. When entering the concentration of the mobile phase ("Conc."), the concentration (in meq./L) of the mobile phase counter-ions of the sample ions must be entered. Exemplary calculations and a list of meq/L. values for common mobile phases are provided in Appendix C to the Operator's Manual in the Appendix. Finally, the total run time ("Time") for the analysis to the tenth of a minute must also be entered. Additionally, as discussed previously, up to ten pre-assigned method parameters may be inputted into the system by following the previous steps.

With respect to an analysis for which the run time is unknown, the operator should enter the longest run time that is considered appropriate for the analysis. After running the analysis, the actual run time may be re-entered by simply depressing the "Select Method" button on the operator interface and scrolling through the parameters as discussed above.

Before accepting a method entered at steps 520–522, the system will check to confirm that the suppressor capacity is sufficient to complete the analysis within 40% of the total run time and that the power supply can generate enough current to complete regeneration within 40% of the total run time. If the suppressor capacity is insufficient, program flow proceeds to step 523 where a message is generated on the system display stating that there is a "cell [e.g. suppressor] type and method mismatch." The operator will either need to replace the suppressors with suppressors having greater capacity, or change the method parameters by reducing the mobile phase concentration, flow rate or run time. The method parameters may be re-set by depressing the "Enter" button on the operator interface at step 523 and program flow will revert back to step 521, where the method parameters may be selected as previously discussed. If the power supply does not have enough current to timely regenerate the suppressor (i.e. within 40% of the run time), program flow proceeds to step 524 where a message is generated on the system display stating that "flow or conc. too high". The operator will need to reduce the mobile phase concentration or the flow rate. As a general rule, the product of the concentration in meq./L and the flowrate in ML/min. should be equal or less than 22.5 (conc.×flowrate<22.5). In any event, the operator may change the parameters relating to mobile phase concentration or the flowrate by depressing the "Enter" button on the operator interface at step 524 and program flow will revert back to step 521, where the method parameters may be selected as discussed.

Based on the foregoing discussion, one skilled in the art will appreciate that the system software will not allow method parameters that exceed 40% of the capacity of the individual suppressors. This limit is to ensure that, regardless of when a sample injection is received by the suppressor system, an individual suppressor will never achieve full exhaustion. For example, a suppressor could have mobile phase flowing through it for almost the entire analysis time before receiving a sample injection. Thus, in a "worst case" scenario, the suppressor could, at most, be nearly 40% exhausted before the sample injection reaches the suppressor. The suppressor, which is 40% exhausted when it finally receives a sample injection, will nonetheless still have 60% of its suppression capacity. Because the system does not accept operating parameters that will exceed 40% of an individual suppressor's capacity, the suppressor will be able to complete the analysis with about 20% of its capacity still remaining. Thus, the suppressor should theoretically never exceed 80% exhaustion in the system. As those skilled in the art will appreciate, in the above-described system, the maximum useful cell capacity is actually 80% of label capacity.

The system further has a variety of pre-programmed sub-routines relating to system errors. For example, if the voltage across a suppressor exceeds a pre-assigned value at any time during regeneration, an error message is generated on the system display at steps 530, 530*a* or 530*b*, depending on what mode of operation the system is in when the error occurs. This message will indicate which of the suppressors in the system has failed, and the system will automatically go into a standby mode. Such an error indicates that there is too much resistance in the suppressor to achieve regeneration within 40% of the sample run time, and the suppressor should be checked. The upper pre-assigned voltage limit is the upper voltage limit of the system power supply. Similarly, if the voltage across a suppressor is below a pre-assigned value at any time during regeneration, an error message is generated on the system display at step 531. Such an error indicates that a short circuit has occurred between the electrodes. In any event, once the voltage problem is corrected, the system power is cycled and program flow reverts back to step 500. Alternatively, the system may be programmed such that, once the voltage problem is eliminated, the program flow reverts back to entry point B by depressing the "Enter" button on the operator interface.

Another error sub-routine is triggered if the cover of the suppressor compartment on the front panel of the unit is open. In such an event, system operation is interrupted and a message is generated on the system display at step 540. A flashing light on the operator interface is triggered as well. If the cover is closed within a pre-assigned period of time, the system will resume operation. If, however, the cover is not closed before passage of this pre-assigned period of time, program flow then proceeds to step 541. Once the cover is closed, program flow then proceeds to entry point A. Alternatively, system operation may be aborted when the cover is open by pressing the "Enter" button at step 540, and program flow proceeds to step 541.

Yet another error sub-routine is triggered if the HPLC pump in the system is either off when the system is powered-up or if the pump shuts down during system operation. In either event, the system goes into a standby mode and a message is generated on the system display at step 550. Once the problem is corrected, program flow proceeds to either entry point A (if the problem occurred while the system was running) or to entry point B (if the system was powered-up with the pump off).

The system is also capable of Remote Out-Put via "Remote Out" pins preferably positioned on the rear panel of the operator interface. The system will send a "Not Ready" signal to external devices such as an automatic sample injection system when the system is not ready to receive a sample injection. The system sends the "Not Ready" signal to external devices until the system is ready to receive a sample injection, which is at step 504. The "Not Ready" signal can also serve as a safeguard if a system failure occurs. Thus, if any of the error sequences discussed above is triggered, a "Not Ready" signal is transmitted to peripheral devices. Additionally, when the system is in the "Full Regen" mode and both suppressors are thus being regenerated, a "Not Ready" signal is likewise sent to external devices.

Conversely, the system is also capable of receiving Remote In-Put via "Remote In" pins preferably positioned on the rear panel of the operator interface. The system may accept an error signal from other external devices. When it receives such an error signal, the system will automatically go into a standby mode.

The preferred columns for the suppressors used in the system are made of a clear, cylindrical shaped, polymethylenepentane material. The electrode and column end fittings comprise a unitary piece. A sintered frit made from an alloy of PEEK and TEFLON is pressed fitted into the end fitting. Such a column is depicted at p. A0000065 of the Appendix.

The above described suppressor unit is preferably used in combination with other external devices in a chromatography system. The other external devices suitable for use with the self-contained suppressor unit discussed above include an HPLC pump capable of low-pulsation solvent delivery with flowrates preferably ranging from 0.01 mL/min. to 10 mL/min. A preferred pump is the ALLTECH Model 526 or Model 426 HPLC pump. Also included in the chromatography system is a detector capable of measuring the analyte. A preferred detector is the ALLTECH Model 550 conductivity detector with a temperature controlled cell compartment adjustable from ambient to 60° C., which eliminates thermally-induced baseline noise and drift. Also included is a strip chart recorder or data system capable of accepting analog voltage data. An autosampler or manual injection valve for sample introduction. An ion chromatography column capable of separating the species of interest. And, optionally, a guard column packed with material similar to the packing in the analytical column.

As can be ascertained from the foregoing discussion, some of the benefits associated with Applicant's system and method are that no separate regenerant reagents or pumps are required and no chemical waste (other than the detector effluent generated on any IC system) is created. The system can be used without fragile membranes and will tolerate high backpressures for greater reliability than membrane-based devices. The system is furthermore compatible with electroactive eluants and organic solvents and operates equally well with all common SIC eluants overcoming the drawbacks associated with prior self-regenerating suppressors.

2. Alternate Valve Schemes

With reference to FIGS. 8C and 8D, an alternative 10-port switching valve scheme is depicted. In FIG. 8C, suppressor 212 is the active suppressor as described previously. Before suppressor 212 is exhausted, the analytical column effluent is re-routed as depicted in FIG. 8D. In FIG. 8D, the suppressor 214 is the active suppressor and the detector effluent is routed from the detector 218 through the 10-port switching valve 210 to suppressor 212 to regenerate the suppressor 212 by electrolysis of the detector effluent as previously described. As those skilled in the art will appreciate, to regenerate the cation exchange resin in either suppressors 212 or 214, it is critical that the anode is located at an inlet (upstream) side of the suppressor.

Figure 9A:
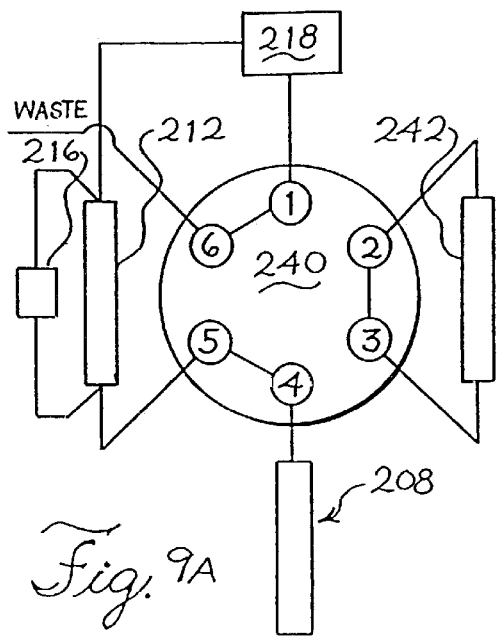
FIGS. 9A and 9B are schematic views of a chromatography apparatus where the column of FIG. 1 is used as a solid phase chemical suppressor.
Figure 9B:
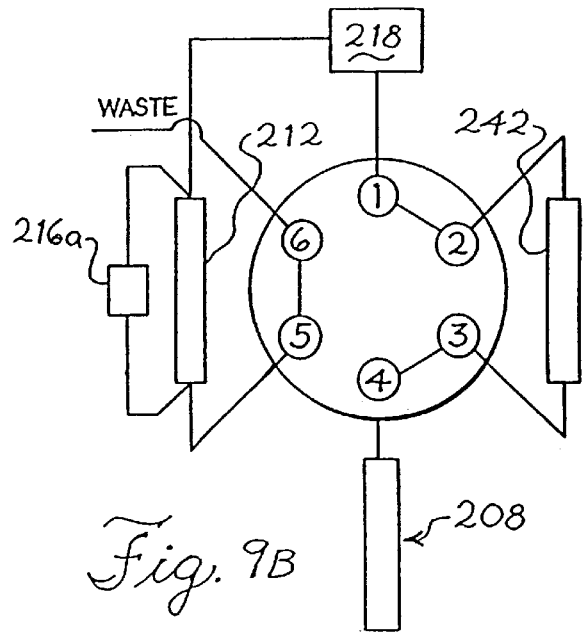

Valve schemes other than the 10-port switching valve described above may also be used in the present invention. With reference to FIGS. 9A and 9B, a 6-port valve 240 may be used. In FIG. 9A, the chromatography effluent is routed from analytical column 208 through 6-port switching valve 240 to suppressor column 212 and to the detector 218 where the sample ions are detected. With reference to FIG. 9B, when the column 212 is exhausted and needs to be regenerated, the 6-port switching valve 240 is switched so the column effluent is routed from analytical column 208 to a packed bed suppressor 242 with strong cation exchange resin in the hydrogen form (i.e., during anion analysis). The cation exchange resin may be as previously described. In the packed bed suppressor 242, the analytical column effluent (aqueous sodium hydroxide or aqueous sodium carbonate/ bicarbonate) is converted to water or carbonic acid. The packed bed suppressor effluent is then routed through the detector 218 to the exhausted column 212, where the water in the packed bed suppressor effluent feeds the electrolysis at column 212 to regenerate the suppressor column 212.

In this scheme, only one suppressor column 212 is used for the analysis. The electrochemical regeneration of the suppressor column 212 can be done between injections, after each injection before the sample anions elute from the analytical column 208, or whenever necessary. The packing material in the packed bed suppressor 242 may be coated with dye to provide color indication of its condition. The packed bed suppressor 242 may need to be replaced only once a month or less depending on its total capacity. Since the packed bed suppressor 242 is not used during the chromatographic analysis, its size is not limited.

Figure 10A:
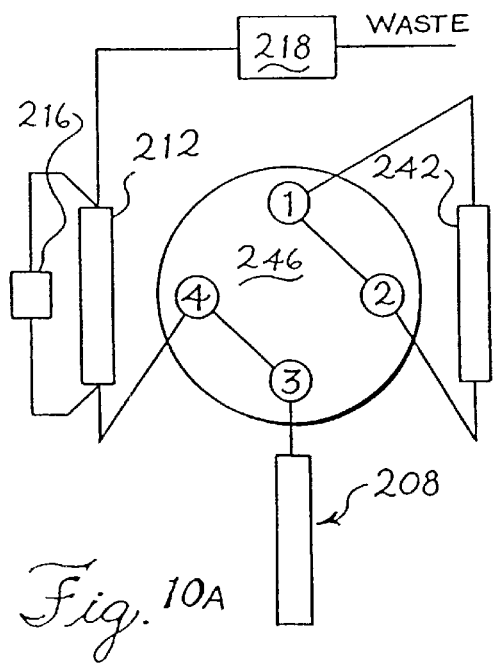
FIGS. 10A and 10B are schematic views of the chromatography apparatus illustrated in FIGS. 9A and 9B, except that a different valve scheme is shown.
Figure 10B:
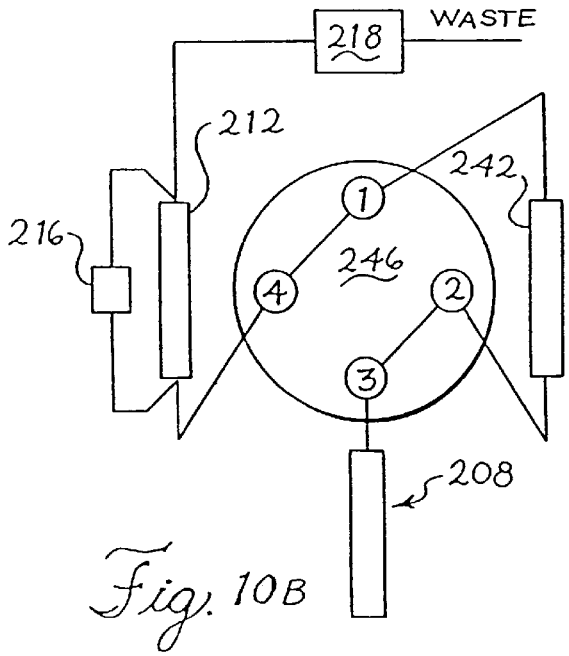

In another aspect of this invention and as depicted in FIGS. 10A and 10B, the system may use a 4-port switching valve 246. In FIG. 10A, the analytical column effluent is routed from the analytical column 820 through 4-port switching valve 246 to suppressor column 212. The suppressor effluent is then routed to the detector 218 (where the sample anions are detected) and then to waste. When the suppressor column 212 is exhausted and needs to be regenerated, the 4-port switching valve 246 is switched so that the analytical column effluent is routed through packed bed suppressor 242 with strong cation exchange resin in the hydrogen form. The analytical column effluent is converted to water or carbonic acid in the suppressor 242. The packed bed suppressor effluent is then routed through 4-port switching valve 246 to column 212 (see FIG. 10B). The water in the packed bed suppressor effluent feeds the electrolysis in column 212 to regenerate the column 212 as previously described. A disadvantage of this design compared to the 6-port switching valve 240 or the 10-port switching valve 210 configurations is that the gases generated during electrolysis will pass through the detector 218 before going to waste. Gas bubbles may thus become trapped inside the detector 218, creating extreme baseline noise.

3. Suppressor for Cation Analysis

As those skilled in the art will appreciate, if the polarity of the previously described suppressor columns are reversed and the chromatography packing materials are changed from cation exchange packing material to anion exchange packing material, the same system configurations as previously described may be used as cation suppressors. In cation analysis, the eluant is usually a solution of an acid such as hydrochloric acid, nitric acid, diaminopropionic acid hydrochloride, or methanesulfonic acid. The anion exchange packing material may be either anion exchange resins or membranes impregnated with anion exchange particles. Preferred anion exchange packing materials include primary, secondary, tertiary, or quaternary amine functionalized inorganic or organic particles. The most preferred anion exchange packing materials comprise quaternary amine functionalized inorganic or organic particles.

In cation analysis, the following reactions take place in the suppressor column (where hydrochloric acid is the eluant and the anion exchange material comprises a quaternary amine functionalized particle):

1) Eluant: $HCl + Resin-NH_4^+OH^- \rightarrow Resin-NH_4^+Cl^- + H_2O$

2) Analyte: $XCl + Resin-NH_4^+OH^- \rightarrow Resin-NH_4^+Cl^- + XOH$ where X=cations (Na, K, Li, Mg, Ca, etc.)

To regenerate the suppressor column in cation analysis, the position of the anode and cathode is opposite of that for anion analysis (i.e., the cathode is placed on the side of the suppressor where the detector effluent enters the suppressor column). During electrolysis, the following reaction takes place at the cathode:

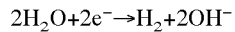

The released hydroxide ions are routed through the column to convert the chloride form resin (exhausted anion exchange material) back to the hydroxide form according to the following reaction:

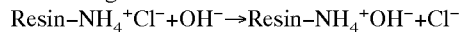

The various valve schemes previously described can also be used for cation analysis.

In yet another embodiment of the present invention, the need for switching between suppressors may be eliminated altogether. Instead of routing the detector effluent through a switching valve to regenerate the non-active suppressor while the active suppressor is in use, the eluant itself may be used to regenerate the exhausted suppressor. In this embodiment, the aqueous eluant is flowed through the separator column to the exhausted (or partially exhausted) suppressor column. Depending on whether cation or anion analysis was just conducted, either hydroxide (cation analysis) or hydronium (anion analysis) ions are generated at the upstream electrode. The hydroxide or hydronium ions are then flowed through the suppressor to convert the suppressor back to either its hydroxide or hydronium form. The advantage to this embodiment is that it eliminates the need for two suppressor columns and the associated switching valves for switching between suppressors. As one skilled in the art will recognize, however, in this embodiment the analyses will be interrupted while regenerating the suppressor. Moreover, the sample counter-ions in the eluant will compete with either the hydronium or hydroxide ions in the suppressor column, and, therefore, total conversion of the exhausted suppressor back to either the hydroxide or hydronium form will not be achieved. However, by controlling current and eluant flow, hydronium or hydroxide conversion can be favored over the sample counter-ions. Although primary adapted for use in a one suppressor system the foregoing method of regenerating a suppressor may also be used to regenerate exhausted suppressors in a system that uses two or more suppressors.

Figure 24:
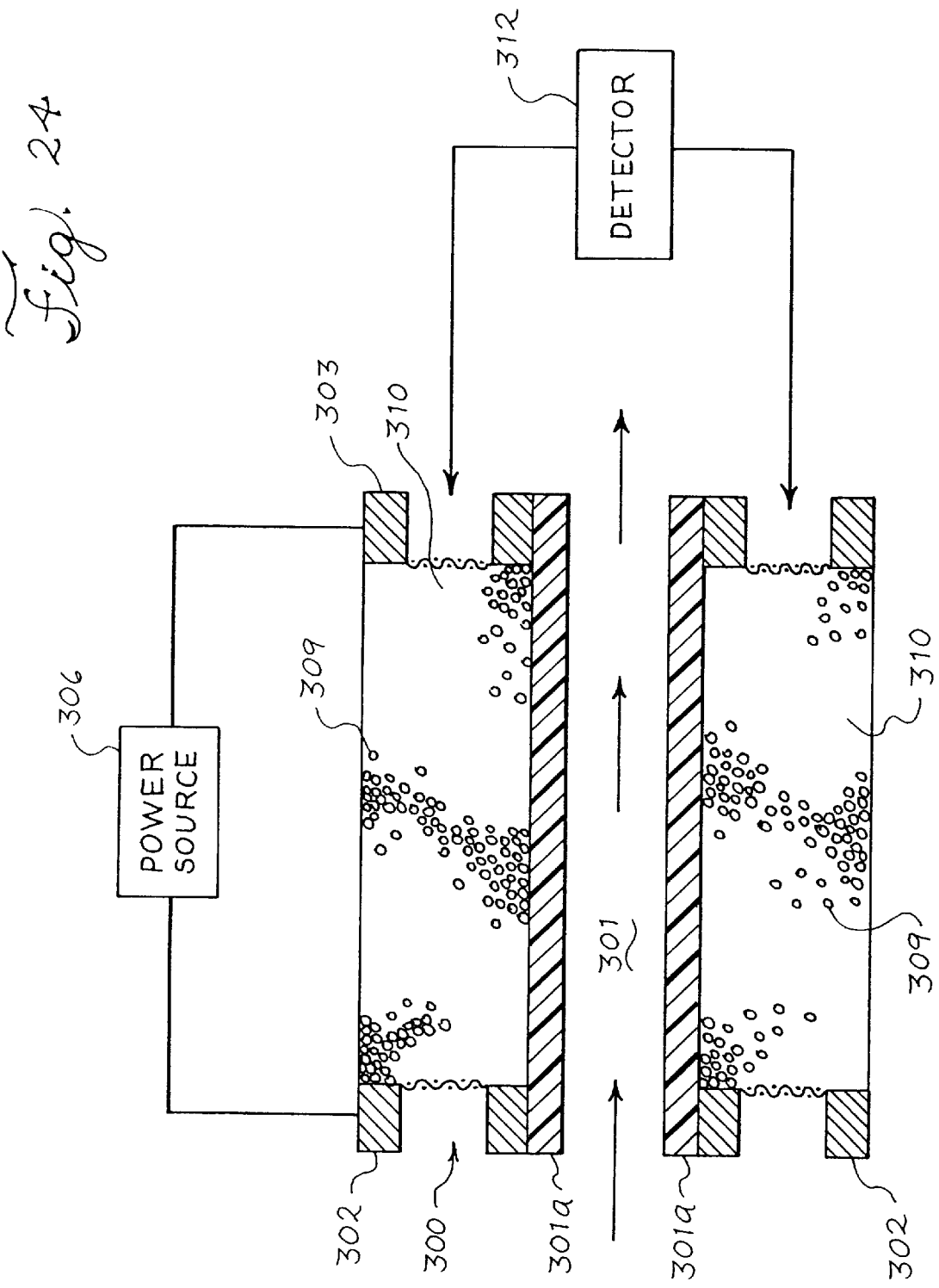
FIG. 24 is a cross-sectional view of a suppressor column according to one aspect of the present invention.

According to yet another embodiment of the present invention, a membrane suppressor is provided. With reference to FIG. 24, a housing 300 is provided comprising a first effluent flow channel 301 defined by a membrane 301a. The membrane 301a is preferably made of Nafion™, which is a semi-permeable plastic material that has been functionalized to contain exchangeable ion sites (not shown) as previously described herein. Annular electrodes 302 and 303 are positioned at the upstream and downstream ends, respectively, of the housing 300. The electrodes may be as previously described. Reinforcing the membrane 301a is ion exchange packing material 309. Aside from reinforcing the membrane 301a to the outward pressure generated by the fluid flowing through channel 301, the packing material 309 also completes a circuit formed by electrodes 302 and 303, power source 306 and ion exchange packing material 309. The ion exchange packing material 309 preferably comprises the same functional groups as the functionalized membrane 301a. According to this embodiment, the suppressor may function as a continuously regenerated membrane suppressor, and will be discussed specifically in reference to anion analysis using an aqueous sodium hydroxide eluant. However, as will be appreciated by those skilled in the art, this embodiment may be easily adapted for cation analysis as well as for use with other inorganic or organic eluants.

With reference to FIG. 24, the membrane 301a preferably comprises exchangeable hydronium ions. Similarly, the reinforcing ion exchange packing material 309 preferably comprises exchangeable hydronium ions. The sample anions and eluant (not shown) are flowed through the first effluent flow channel 301 wherein the counter-ions ($Na^+$ in this example) of the sample anions displace the hydronium ions on the membrane 301a. Displaced hydronium ions combine with the sample anions to form the highly conductive acids of the sample anions. Similarly, displaced hydronium ions combine with the eluant co-ions of the sample ions (e.g., $OH^-$ in this example) to form the less conductive water. The sample anions (in their acid form) and water are flowed to the detector where the sample ions are detected. The detector effluent or another external source of water-containing solution is then routed through a second effluent channel 310 while power source 306 is turned on. An electric current across the ion exchange packing material 309 is generated. The upstream electrode 303 functions as the anode and the water in the detector effluent is electrolyzed to yield, among other things, hydronium ions. The hydronium ions may then migrate through the packing material 309 to the membrane 301a where the hydronium ions displace the sodium ions on the membrane 301a. By keeping the power supply 306 turned on, a continuous supply of hydronium ions may be generated at electrode 303 and continuously supplied to membrane 301a thereby maintaining the membrane 301a in a suppressing form indefinitely. As those skilled in the art will appreciate, the housing 300 may be tube-shaped such that the packing material 309 is concentric with the membrane 301a. Alternatively, the housing may be rectangular shaped such that the packing material 309 is adjacent the planar shaped membranes 301a on the side of the membrane opposite channel 301. Additionally, packing material 309 may also be positioned in channel 301 for increased suppressor capacity and for further supporting membrane 301a to prevent membrane rupture.

4. High Purity Eluant Chromatography

The column illustrated in FIG. 1 can also be advantageously employed in a method and apparatus for generating a high purity eluant. With reference to FIG. 11A, a deionized water source 100 is provided. A pump 102 as previously described is connected to water source 100. Downstream from pump 102 is a sample injector 104. Downstream from the sample injector 104 are three columns 112, 120 and 122, which are arranged in series. Column 112 is preferably constructed as illustrated in FIG. 1. An electrical power source 116 is connected to column 112. Column 120 is an analytical (e.g. chromatography) column packed with chromatography packing material (not shown). Column 122 is also preferably constructed as illustrated in FIG. 1, and is adapted for use as a solid-phase chemical suppressor in this embodiment. Located downstream from columns 112, 120 and 122 is a conductivity detector 118, which is as previously described. Finally, downstream from detector 118, is a backpressure valve 144 and an ion exchange bed 146, which are also as previously described.

For anion analysis, column 112 is adapted for use as an eluant generating source and is packed with cation exchange packing material (not shown). The packing material preferably comprises exchangeable sodium ions. Column 120 is packed with anion exchange packing material (not shown) which is selected as previously described. Finally, column 122 is packed with cation exchange packing material (not shown) comprising exchangeable hydronium ions, and is selected as previously described. The electric power source 116 is connected to an anode (not shown) which is positioned at the upstream end of column 112, and a cathode (not shown) which is positioned at the downstream end of the column 112. A high purity eluant for anion analysis is generated as follows.

The water-containing eluant is routed through eluant generating column 112. Power source 116 is turned on thereby generating an electric current sufficient to electrolyze water across the sodium form cation exchange packing material (not shown) in column 112. At the anode (not shown), which is located at the upstream end of column 112, the water-containing eluant undergoes electrolysis thereby generating hydronium ions as previously described. At the cathode (not shown), which is located at the downstream end of column 112, the electrolysis of the water-containing eluant generates hydroxide ions as previously described. The hydronium ions generated at the upstream end of the column 112 flow across the sodium form cation exchange packing material and displace the sodium ions. The released sodium ions combine with the hydroxide ions generated at the downstream end of the column 112 to form a high purity sodium hydroxide eluant.

The sample anions (which may be injected either before or after eluant generating column 112), and the high purity sodium hydroxide eluant are then routed through analytical column 120, where the sample anions are then separated. The analytical column effluent is then routed from column 120 to solid phase chemical suppressor 122. The sample anions are converted to their highly conductive acids by exchanging their counterions for the hydronium ions on the hydronium form cation exchange packing material in suppressor 122. Similarly, the sodium hydroxide eluant is converted to relatively non-conductive water by exchanging its sodium ions for the hydronium ions on the hydronium-form cation exchange material in suppressor 122. The suppressor effluent is then routed from suppressor 122 to detector 118 where the sample anions are detected. The detector effluent is then routed through back-pressure regulator 144 to ion exchange bed 146. For anion analysis, ion exchange bed 146 comprises anion exchange packing material comprising exchangeable hydroxide ions, and is selected as previously described. The sample anions displace the hydroxide ions in the ion exchange bed 146. The released hydroxide ions combine with the hydronium counterions of the sample anions to form water. The water may then be routed back to water source 100.

As those skilled in the art will appreciate, in addition to generating a high purity eluant, the foregoing method can suitably be used in a method of gradient elution chromatography by controlling the amount of sodium hydroxide eluant generated in column 112. The higher the current in column 112, the greater the concentration of sodium hydroxide that will be generated in column 112.

When columns 112 and 122 are exhausted, i.e. the ion exchange packing material is converted to the hydronium form and sodium form, respectively, they may be regenerated, either on-line or off-line. On-line regeneration may be accomplished according to the following steps. With reference to FIG. 11B, the water-containing eluant is rerouted and routed to column 122. An electrical power source 123 is provided. The power-source 123 is connected to an anode (not shown), which is positioned at the upstream end of column 122, and a cathode (not shown) which is positioned at the downstream end of column 122. The water-containing eluant enters column 122 at the anode (not shown) end of column 122. Power source 123 is turned on thereby generating an electric current sufficient to electrolyze water across the cation exchange packing material (now in the sodium form) in column 122. Hydronium ions are generated at the anode end of column 122 by the electrolysis of the water-containing eluant as previously described. Also, hydroxide ions are generated at the cathode end of the column 122 by the electrolysis of water as previously described. The hydronium ions are routed across the sodium form cation exchange material in column 122 and displace the sodium ions thereby converting the cation exchange resin back to the hydronium form. The released sodium ions and the excess hydronium ions generated at the anode end of column 122 combine with the hydroxide ions generated at the cathode end of column 122 to form a high purity sodium hydroxide and water eluant.

The high purity sodium hydroxide eluant (as well as any sample anions to be detected) is routed through analytical column 120, where any sample anions are separated as previously discussed, and then to column 112. The exhausted cation exchange packing material in column 112 is in hydronium form. The hydronium ions on the exhausted cation exchange material in column 112 are displaced by sodium ions in the sodium hydroxide eluant thereby regenerating the cation exchange packing material back to its sodium form. The released hydronium ions combine with the hydroxide ions in the eluant to form relatively low conductivity water. The water (and sample anions) may then be routed to a detector (not shown) where the sample anions are detected. The detector effluent may then be routed through an ion exchange bed (not shown) where the sample anions are retained and hydroxide ions are released and combine with the hydronium counterions of the sample anions to form water as previously described. The water may then be routed to the water source 100.

The foregoing method and apparatus can also be used for generating a high purity eluent for cation analysis. In this embodiment, the column 112 is packed with anion exchange packing material, preferably comprising exchangeable chloride ions. Column 120 is packed with cation exchange packing material preferably comprising exchangeable hydronium ions, and suppressor column 122 is packed with anion exchange packing material comprising exchangeable hydroxide ions.

FIG. 11C is a schematic of an alternative method and apparatus for generating a high purity eluent and capable of a gradient. In this embodiment, the eluant generating column 113 may comprise a disposable cartridge packed with either anion or cation exchange packing material as previously described with respect to eluant generating column 112 (see FIG. 11a and accompanying text in specification). Also, the sample is injected downstream from the eluant generating column 113.

In yet another embodiment of the present invention, salt gradients may be achieved using the principles of the present invention. For example, two columns as illustrated in FIG. 1 may be placed in series; one column packed with cation exchange packing material (i.e., the cation column) and the other column packed with anion exchange packing material (i.e., the anion column). Eluant is flowed through the columns while a current is applied in these columns as previously discussed. Hydronium ions are generated at the upstream electrode of the cation column and are flowed through the cation column so as to replace the cations in the cation column. Similarly, hydroxide ions are generated at the upstream electrode of the anion column and are flowed through the anion column so as to replace the anions in the anion column. The cations released from the cation column and the anions released from the anion column combine to form a salt. Thus, for example, a relatively pure salt gradient of sodium chloride may be generated by packing the cation column with exchangeable sodium ions and packing the anion column with exchangeable chloride ions. As those skilled in the art will appreciate, a sodium chloride gradient is desirable for separating species such as protein, which have somewhat neutral pH and relatively high ionic strength. Also, when exhausted, these cation and anion columns may be regenerated as previously discussed.

5. Combination with Hydrophobic Packing Material (Hydrophobic Suppressor)

The column illustrated in FIG. 1 can also be used with a hydrophobic suppressor column, which is particularly useful in methods of inorganic anion analysis using an organic anion as the eluant. With reference to FIG. 12A, the sample anions and the eluant (which comprises an organic anion) are routed through analytical column 8. The analytical column 8 is packed with anion exchange packing material (not shown) as previously described. The sample anions are thus separated in the analytical column 8 according to methods known by those skilled in the art.

The analytical column effluent is then routed to suppressor column 12, which is preferably constructed as illustrated in FIG. 1 and which is packed with cation exchange packing material (for anion analysis). The cation exchange packing material preferably comprises exchangeable hydronium ions (not shown) as previously described. The organic anion eluant is converted to its organic acid form by ion exchange with the cation exchange packing material in suppressor column 12. Similarly, the sample anions are converted to their highly conductive acid form by ion exchange with the cation exchange packing material in column 12.

Thus, two of the ion-exchange reactions that take place in the suppressor column 12 are:

1) Eluant: $Na+\text{-Organic Anion-}+Resin-SO_3^-H^+$
   $\rightarrow Resin-SO_3^-Na^+ + \text{Organic Acid}$
2) Analyte: $NaX + Resin-SO_3^-H^+ \rightarrow Resin-SO_3^-Na^+ + HX$
   where X=anions (Cl, $NO_2$, Br, etc.)

The suppressor column effluent is then routed through a hydrophobic suppressor 50b, which is packed with organic or inorganic reversed-phase packing material (not shown), and preferably with organic reversed phase packing material. The preferred reversed-phase packing material comprises polystyrene divinyl benzene copolymer. The organic acid eluant is adsorbed on the packing material in column 50b and retained. The inorganic sample anions (which are in their acid form) are not adsorbed by the hydrophobic suppressor 50b and are routed to conductivity detector 18 as high conductivity acids in a stream of water where they are detected. This device significantly increases signal to noise ratios, just as other suppressors do, but may be used with a much wider range of eluants, columns and methods.

The combination of the column of the present invention with a hydrophobic suppressor can be used to construct continuously-regenerable hydrophobic suppressor units 52a and 52b as illustrated in FIGS. 12A and 12B.

The system depicted in FIGS. 12A and 12B will function properly until either the cation exchange packing material in columns 12 or 14 become exhausted (converted to the sodium form) or until the capacity of the hydrophobic suppressors 50a or 50b to adsorb the eluant organic acid is exceeded. The relative bed sizes for the suppressor columns 12 and 14 and the hydrophobic suppressors 50a and 50b are preferably chosen so that the capacity of the suppressor columns 12 and 14 are exceeded before that of the hydrophobic suppressors 50a or 50b.

With reference to FIGS. 12A and 12B, two such hydrophobic suppressor units 52a and 52b, respectively, may be used in any of the valve arrangements previously described. Before the first hydrophobic suppressor unit 52a is exhausted, the valve 10 is switched (see FIG. 12B) and the detector effluent is re-routed through the exhausted hydrophobic suppressor unit 52b. The detector effluent contains the sample inorganic anions in their acid form and water. The water in the detector effluent is used to feed electrolysis for regenerating the exhausted hydrophobic suppressor unit 52b. This is accomplished as follows.

The detector effluent is routed to suppressor column 12 and power source 16b is turned on to generate an electric current sufficient for the electrolysis of water across the exhausted cation exchange packing material in column 12. The anode is located at the upstream end of the suppressor column 12. Hydronium ions are thus generated at the upstream side of suppressor column 12 as previously described. The hydronium ions are routed through column 12 and displace the sample and eluant counterions on the exhausted cation exchange packing material thereby regenerating the packing material. The hydroxide ions generated at the cathode, which is located at the downstream end of the suppressor column 12, combine with the released sample and eluant counterions from the column 12 to form their hydroxides.

These hydroxides are then routed through the hydrophobic suppressor 50b before going to waste. It is well known that organic acids in their ionized state are very poorly adsorbed by hydrophobic packing materials. Thus, as the hydroxides are routed through the hydrophobic suppressor 50b, the strongly adsorbed organic acids are converted back to their weakly adsorbed ionized salts causing them to desorb from the hydrophobic suppressor 50b. The hydrophobic suppressor effluent is then routed to waste through 10-port valve switch 210. In this way, both the hydrophobic suppressor 50b and the suppressor column 12 are simultaneously regenerated.

A similar configuration can be envisioned for hydrophobic suppression in cation analysis, except that the polarity of the suppressor columns 12 and 14 are reversed, the suppressor columns are packed with anion exchange packing material comprising exchangeable hydroxide ions. The same hydrophobic suppressor packing material as previously described for anion analysis, however, may be used for cation analysis as well.

6. Other Applications

As those skilled in the art will readily appreciate based on the foregoing disclosure, the columns and methods of the present invention can be used in a variety of other applications as well. For example, the column illustrated in FIG. 1 can be used as a sample pretreatment device to reduce the pH of basic samples or to increase pH of acidic samples. The columns of the present invention can be packed with cation exchange packing material in the hydrogen form as previously described and can be used to reduce sample pH, removing hydroxide or carbonate. When the cation exchange packing is exhausted, it can be electrochemically regenerated as previously described. Conversely, the columns of the present invention can be packed with anion exchange packing material as previously described to increase sample pH or remove hydrogen ions. When the anion exchange packing material is exhausted, it can be electrochemically regenerated as previously described.

The column illustrated in FIG. 1 can also be used for other post column reactions that are pH-dependent. For example, the columns of the present invention can also be used to regenerate solid phase reagent (SPR) suppressors. In SPR, an aqueous suspension of submicron size resin is added post-column to the eluant stream to chemically suppress the eluant. U.S. Pat. No. 5,149,661 provides a detailed discussion of SPR, the disclosure of which is fully incorporated by reference herein. By using the column and methods of the present invention to perform electrolysis on the detector effluent, the released hydrogen or hydroxide ions can electrochemically regenerate the reagent and it can be recirculated on-line.

The column illustrated in FIG. 1 may also be adapted as a preconcentration device for ion analysis. The column may be packed with any of the chromatography packing materials previously described. Samples containing components with a strong attraction to the chosen packing may be routed through the column where they will be retained on the packing contained therein. Thereafter, water may be routed through the column and power supplied to elute the sample as previously described. Very large volumes of dilute samples may be passed through the column. The retained sample mass may be electrochemically eluted in a much smaller volume and at a much higher concentration greatly aiding subsequent separation and/or detection by, for example, chromatography, atomic adsorption, ICP, or mass spectrometry.

As those skilled in the art will appreciate based on the foregoing disclosure, the apparatuses and methods of the present invention are based on electrochemically modifying the mobile phase (e.g., the eluant) to modify the retention of a compound or species on the stationary phase (e.g., the chromatography material). Thus, the inventions and apparatuses of the present invention are not limited to the use of water-containing eluants. Indeed, any eluant that can be electrochemically modified is contemplated for use in the methods and apparatuses of the present invention. For instance, eluants containing non-aqueous species are also suitable for use in the present invention. Suitable non-aqueous species include alkyl, aromatic and olefinic alcohols, halogens, and thiols; aromatics in the presence of a nucleophile; and organic acids, sulfuric and nitric acids (non-aqueous). However, where such non-aqueous species are used as the eluant, catalytic electrodes may be required. For example, where methyl alcohol (e.g., methanol) is used as the eluant, the following reactions take place at catalytically active rheuthenium cyanide electrodes:

Anode: $CH_3OH \rightarrow 2H^+ + CH_2O + 2e^-$

Cathode: $CH_2O + 2e^- + H^+ \rightarrow CH_3OH$

Thus, as those skilled in the art will readily appreciate, by electrochemically modifying the mobile phase (e.g., the eluant), the environment within the effluent flow channel may be modified which thereby modifies the retention or affinity of the compound or species retained on the chromatography material in the effluent flow channel.

Finally, the methods and columns of the present invention have other, far-reaching applications outside of the chromatography field. For example, the methods and apparatuses of the present invention can be applied to achieve a self-regenerating home water-softening system. For example, suitable chromatography packing materials (such as the ion-exchange packing materials previously described) can be used to remove cations (e.g. hardness) from the water. Once the chromatography packing material is exhausted, it can be regenerated as previously described by the electrolysis of water.

In order to illustrate certain embodiments of the present invention, the following examples are provided. However, the examples should not be construed as to limiting the present invention, the scope of which is defined by the appended claims and their equivalents.

EXAMPLE 1

Figure 13:
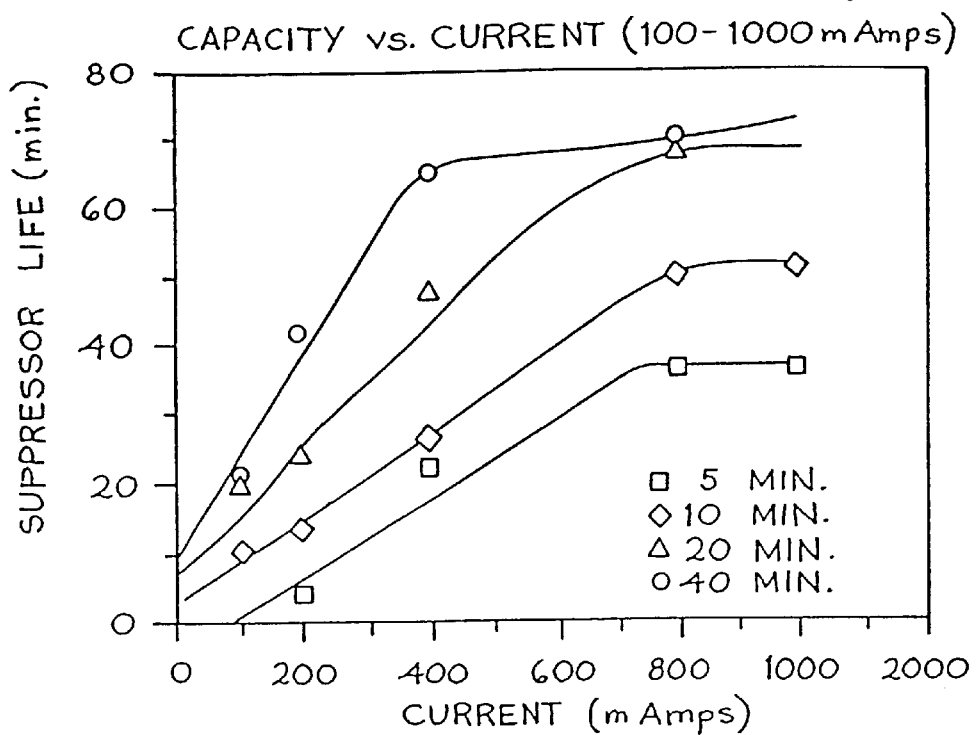
FIG. 13 is a graph illustrating the suppression capacity of a column according to one embodiment of the present invention.
Figure 14:
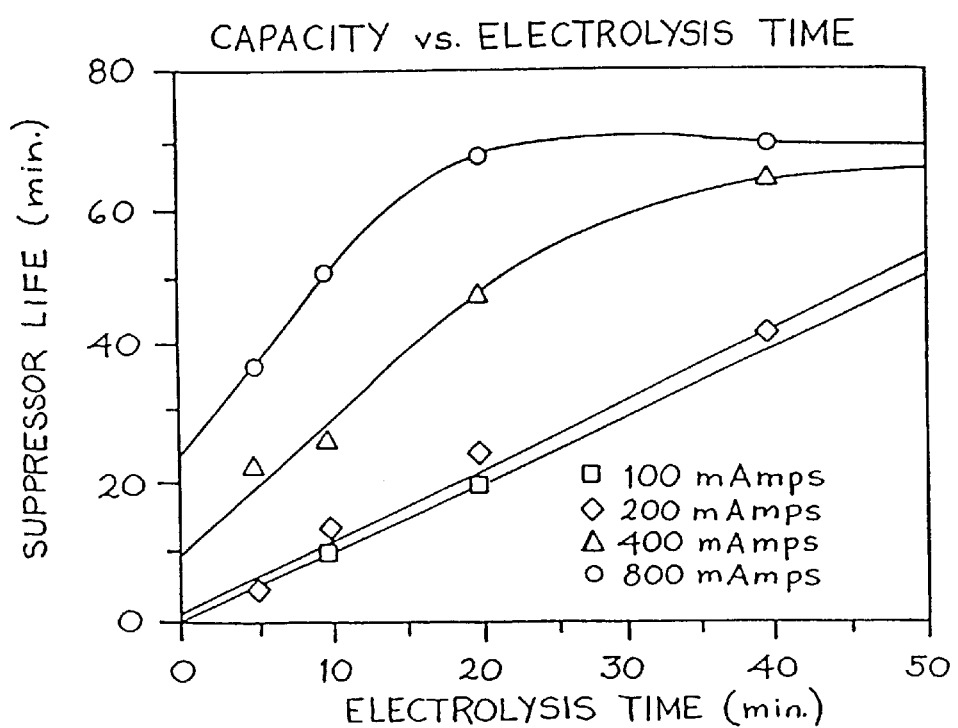
FIG. 14 is a graph illustrating the suppression life of a column according to one embodiment of the present invention.

Relationship Between Current, Regeneration or Electrolysis Time, and Suppressor Capacity or Lifetime FIG. 13 shows the relationship between the suppressor capacity of a column according to the present invention and the applied current during regeneration. The voltage applied across the column during the electrolysis is between 3–5 V. FIG. 14 shows the relationship between suppressor capacity and electrolysis regeneration time. These results show that there is a linear relationship between electrolysis time, current, and suppressor capacity. Several of the curves in FIGS. 13 and 14 have slopes greater than 1 demonstrating that the column of the present invention can be electrochemically regenerated in less time than it takes to exhaust during use. This is required for cycling between two columns to work.

EXAMPLE 2

Reproducibility of the Regeneration Process

When three electrolysis regenerations were performed repeatedly on the same column (10 minute electrolysis at 400 mAmps (¾" diameter opening)), the following results were obtained:

| Trial # | Suppressor Capacity (min) |
|---------|---------------------------|
| 1       | 129                       |
| 2       | 130                       |
| 3       | 132                       |

These results indicate that the regeneration process is consistent and reproducible.

EXAMPLE 3

Chromatography

Figure 15:
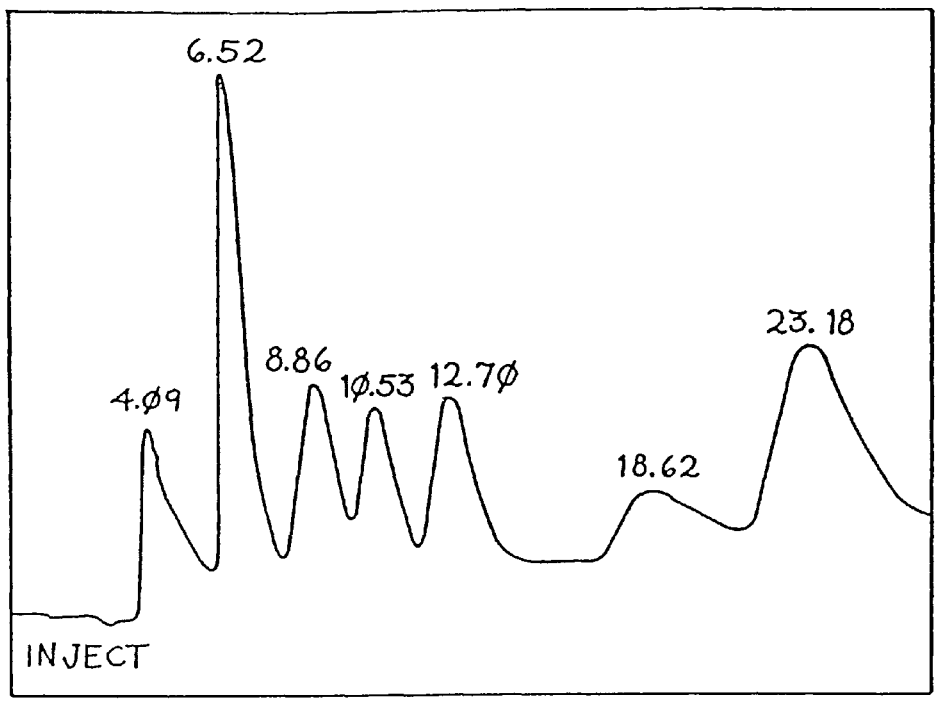
FIG. 15 is a chromatogram of a sample containing ions using a column according to one embodiment of the present invention.
Figure 16:
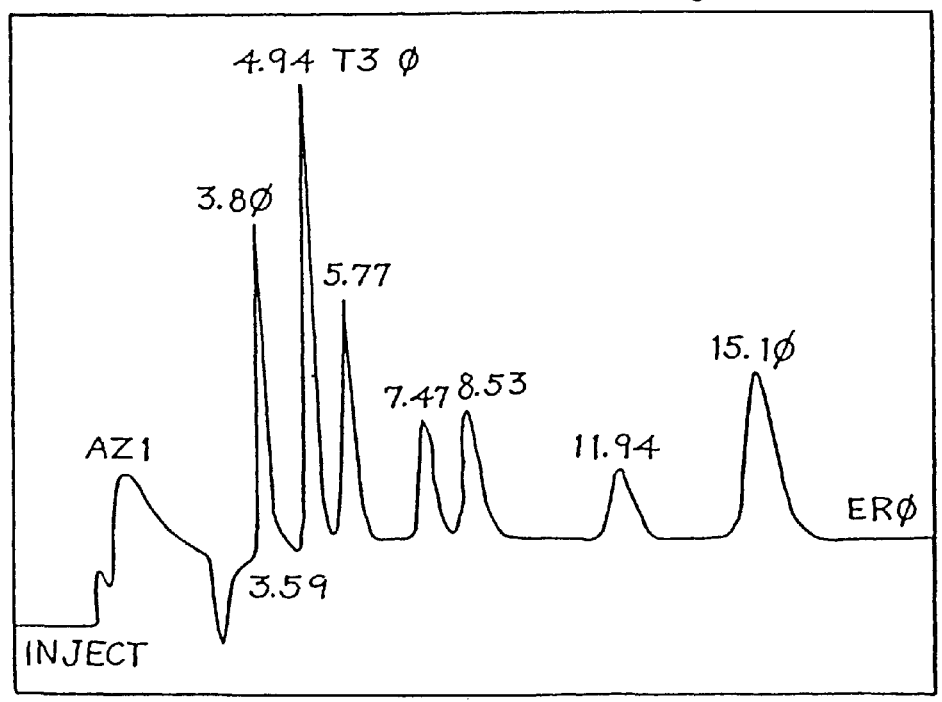
FIG. 16 is a chromatogram of a sample containing ions using a column according to one embodiment of the present invention.

FIG. 15 shows a chromatogram of anions obtained using the column of the present invention as a suppressor with 1" diameter column packed with sulfonic-acid functionalized polystyrene-divinyl benzene cation exchange packing material. The peaks are broad due to band broadening, resulting in loss of chromatographic efficiency. The band broadening is due to the large void volume in the suppressor column. FIG. 16 shows a chromatogram of anions obtained using 0.75 cm diameter cell packed with the same cation-exchange packing material. By reducing the bed diameter, band broadening is reduced.

EXAMPLE 4

Electroelution Ion Chromatography (Anion Analysis)

The following materials and conditions were used in this example:
Column: 6 mm×7.5 mm packed with anion-exchange functionalized organic particles (trimethylammonium functionalized divinylbenzene polymer)
Eluant: Deionized water
Flow rate: 1.0 mL/min.
Detector: 350 conductivity detector
Sample: Anion (fluoride, chloride)
Electrolysis: Constant Voltage
Results:
FIG. 17 shows a separation of fluoride and chloride obtained on this column. The electrolysis was conducted at 28 V. A backpressure regulator of 100 psi was installed at the detector outlet to reduce bubble formation from the generation of $O_2(g)$ and $H_2(g)$ during the electrolysis.

EXAMPLE 5

Cation Analysis Using Electrochemically Regenerated Suppressor Column

The following materials and conditions were used:
Suppressor: Suppressor A—7.5 mm ID×0.9 mm thick
Suppressor B—10 mm ID×0.31" thick
Amount of packing: Packed with 0.40 grams anion exchange resin in hydroxide form (trimethylammonium functionalized polystyrene-divinylbenzene polymer) (Suppressors installed in 10-port Micro-Electric Actuator)
Column: ALLTECH Universal Cation Column (polybutadiene-maleic acid coated silica particles)
Eluant: 3 mM Methane Sulfonic Acid
Flow rate: 1.0 mL/min.
Detector: 350 Conductivity Detector
Sample: injections (A) lithium, (B) sodium, (C) ammonium, (D) potassium, (E) magnesium, (F) calcium, 50 µL injection
Electrolysis: Constant current at 79 mAmps
Results:
FIG. 18 shows a separation of cations obtained using a column according to the present invention as a suppressor for cation analysis.

EXAMPLE 6

Electroelution Ion Chromatography (Cation Analysis) With Water Containing Eluant The following materials and conditions were used:
Column: 30 mm×4.6 mm packed with ALLTECH Universal Cation Column (polybutadiene-maleic acid coated silica particles)
Eluant: Deionized water containing 0.1 mm methane sulfonic acid
Flowrate: 1.0 mL/min
Detector: model 350 conductivity detector Sample: lithium, sodium, ammonium, potassium Results:

Deionized water was used as the eluant originally. Since a much longer column (30 mm-very high resistant) was used, the power supply (this power supply has 36V upper limit) was not able to generate current for electrolysis. No elution of cations was observed. A small amount of methane sulfonic acid was added to the water to reduce the resistance of the water eluant.

Figure 19:
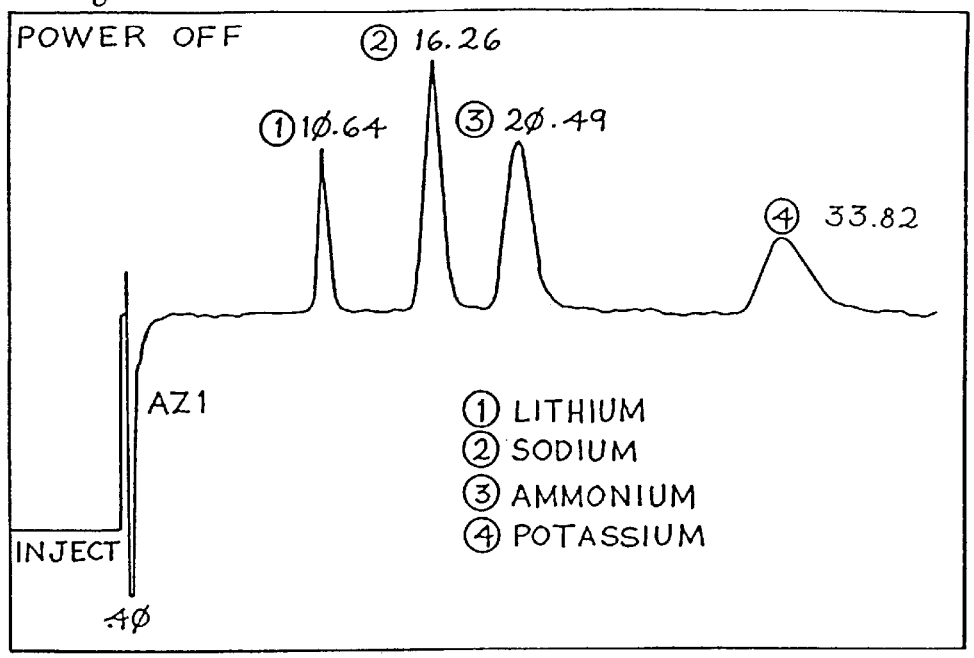
FIG. 19 is a chromatogram of a sample containing ions using a column according to one embodiment of the present invention.
Figure 20:
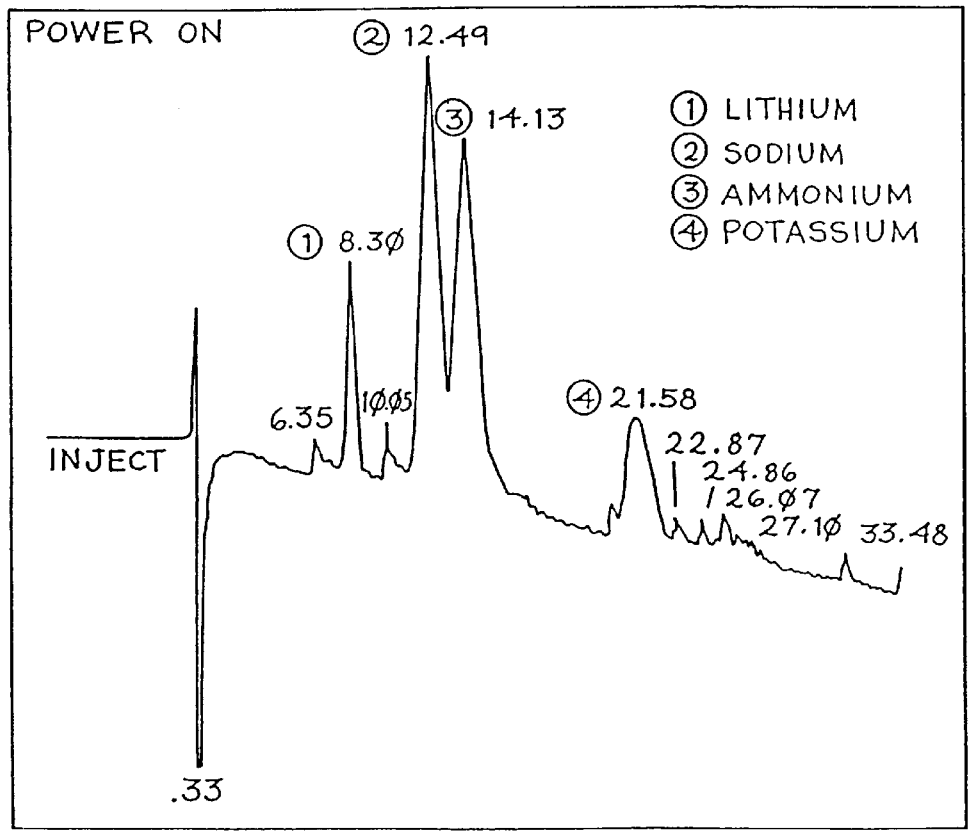
FIG. 20 is a chromatogram of a sample containing ions using a column according to one embodiment of the present invention.

FIG. 19 shows the separation of the 4 cations with just the 0.1 mm methane sulfonic acid and water as the eluant (power supply was turned off). FIG. 20 shows the same separation with the power on. The peaks are eluted at much shorter time in FIG. 20. Thus, when the concentration of the hydronium ions is increased by generating an electric current in the column, the sample cations are eluted faster. The electrolysis was conducted at 28V. As depicted in FIG. 20, some baseline noise was detected in the analysis, which was caused by the bubbles formed during electrolysis of water. A backpressure regulator was not used in this analysis.

EXAMPLE 7

Gradient Electroelution Ion Chromatography
(Anion Analysis)

The following materials and conditions were used in this example:

Column: 6 mm×7.5 mm column packed with anion exchange functionalized organic particles (trimethylammonium functionalized divinylbenzene polymer)

Eluant: Deionized water

Flowrate: 1.0 mL/min

Detector: model 350 conductivity detector

Sample: fluoride (5 ppm), chloride (10 ppm), nitrate (10 ppm); 50 μm injection

Figure 21:
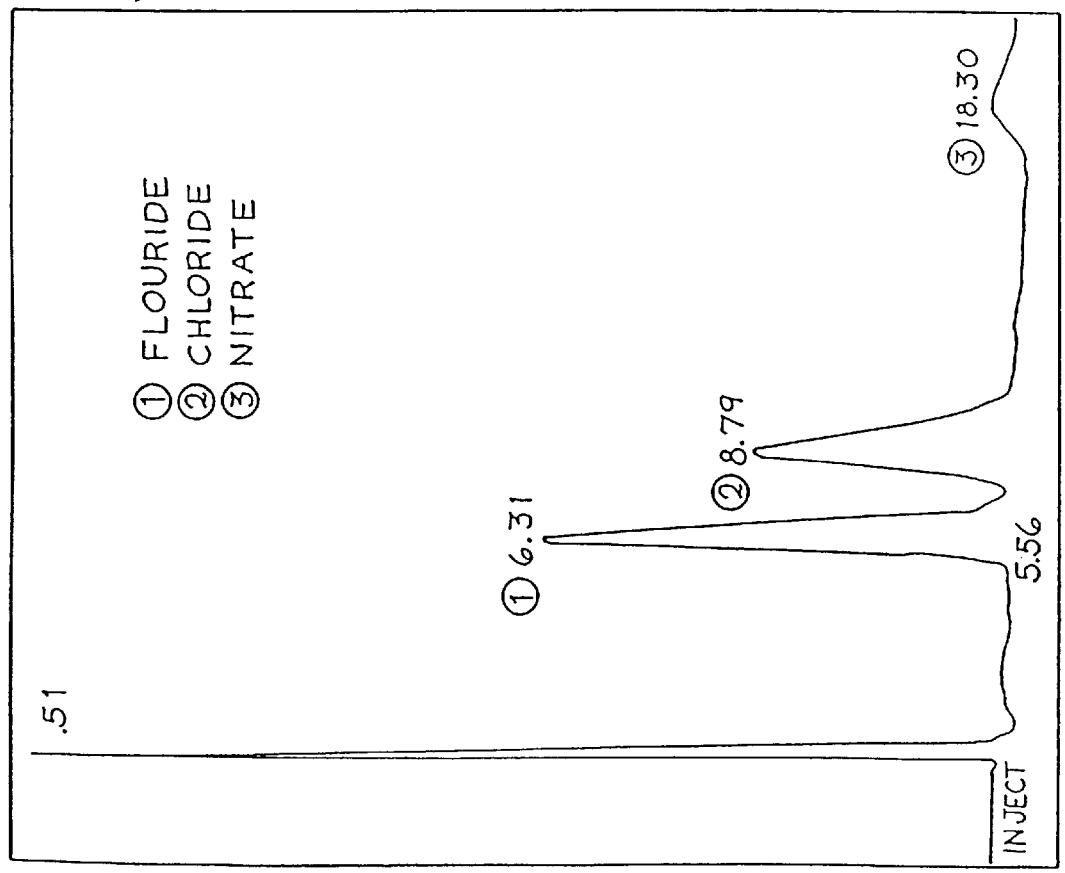
FIG. 21 is a chromatogram of a sample containing ions using a column according to one embodiment of the present invention.
Figure 22:
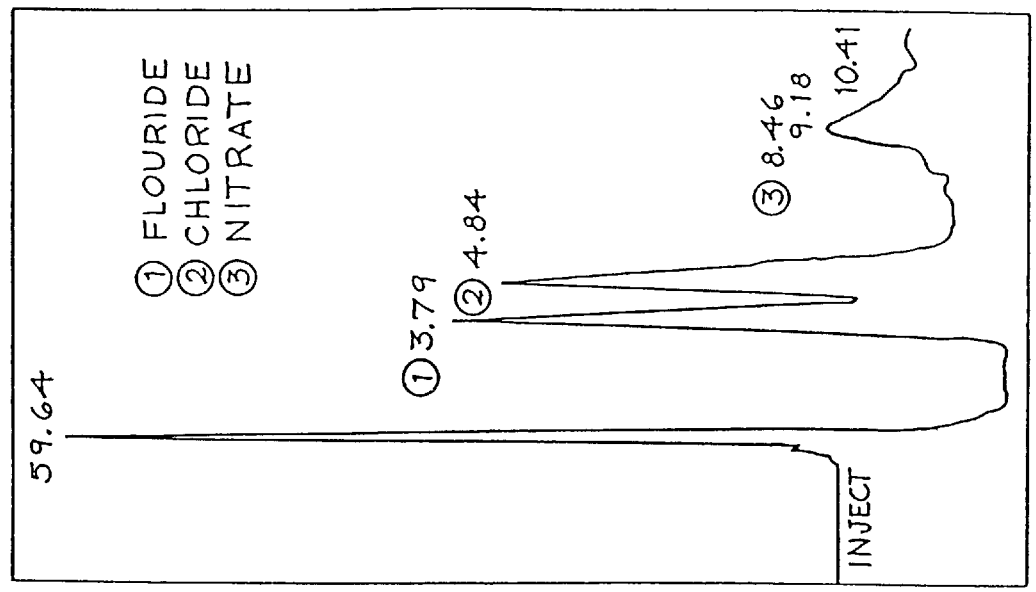
FIG. 22 is a chromatogram of a sample containing ions using a column according to one embodiment of the present invention.

Results:

FIG. 21 shows a separation of fluoride, chloride, and nitrate obtained on this column with constant current electrolysis at 10 mAmp. The retention time for fluoride, chloride, and nitrate are 6.31, 8.79, and 18.3 minutes, respectively. FIG. 22 shows the separation of the same components on this column with constant current electrolysis at 16 mAmp. By increasing the current, the retention time for all anions is reduced. These results indicate that the amount of hydroxide ions produced during electrolysis is proportional to the amount of current used. By varying the electric current during the separation, the concentration of the eluant may be varied, thereby generating a gradient.

We claim:

1. A method of generating a high purity eluant for detecting sample ions comprising:

providing a water source;

providing an eluant generating source comprising counter-ions of the sample ions and a fluid flow path for liquid flow through the eluant generating source, the fluid flow path in liquid communication with the water source, wherein the fluid flow path is the only path for liquid flow through the eluant generating source;

flowing water to the eluant generating source and performing electrolysis of the water in the fluid flow path to generate electrolysis ions having the opposite charge of the sample counter-ions wherein the electrolysis ions are selected from the group consisting of hydronium ions and hydroxide ions;

combining the electrolysis ions with the sample counter-ions to form a high purity eluant;

flowing the sample ions and the high purity eluant through an analytical column to separate the sample ions; and flowing the separated sample ions to a detector where the sample ions are detected.

2. The method of claim 1 wherein the sample ions comprise anions, the sample counter-ions comprise cations and the electrolysis ions comprise hydroxide ions.

3. The method of claim 2 wherein the sample counter-ions comprise sodium.

4. The method of claim 1 wherein the sample ions comprise cations, the sample counter-ions comprise anions and the electrolysis-ions comprise hydronium ions.

5. The method of claim 4 wherein the sample counter-ions comprise chloride.

6. The method of claim 1 wherein an electrode is in liquid communication with the fluid flow path.

7. The method of claim 1 wherein the sample ions and high purity eluant are flowed through a suppressor, wherein the suppressor is positioned downstream from the analytical column and upstream of the detector in the path of fluid flow.

8. A system for detecting sample ions using a high purity eluant comprising:

a water source;

an eluant generating source comprising counter-ions of the sample ions and a fluid flow path for liquid flow through the eluant generating source, the fluid flow path in liquid communication with the water source, wherein the fluid flow path is the only path for liquid flow through the eluant generating source;

an analytical column in liquid communication with the fluid flow path and positioned downstream from the eluant generating source in the path of fluid flow; and a detector in liquid communication with the fluid flow path and positioned downstream from the analytical column in the path of fluid flow.

9. The system of claim 8 wherein the fluid flow path in the eluant generating source is in liquid communication with chromatography material.

10. The system of claim 9 wherein the chromatography material comprises cation exchange resin.

11. The system of claim 10 wherein the cation exchange resin is impregnated in a membrane.

12. The system of claim 9 wherein the chromatography material comprises anion exchange resin.

13. The system of claim 12 wherein the anion exchange resin is impregnated in a membrane.

* * * * *

UNITED STATES PATENT AND TRADEMARK OFFICE
CERTIFICATE OF CORRECTION

PATENT NO. : 6,558,551 B1
DATED : May 6, 2003
INVENTOR(S) : James M. Anderson, Jr. et al.

It is certified that error appears in the above-identified patent and that said Letters Patent is hereby corrected as shown below:

Title page,
Item [56], References Cited, OTHER PUBLICATIONS, delete "Mat'tsev" and substitute -- Mal'tsev -- in its place.

Column 39,
Line 51, insert -- introducing the sample into the fluid flow path and flowing the sample ions through the eluant generating source -- after "generating source" and before ";" (semicolon).

Column 40,
Line 23, delete "electrolysis-ions" and substitute -- electrolysis ions -- in its place.
Line 39, insert -- a sample injector for injecting sample ions upstream of the eluant generating source -- after "generating source" and before ";" (semicolon).

Signed and Sealed this

Twenty-second Day of June, 2004

JON W. DUDAS
*Acting Director of the United States Patent and Trademark Office*